US012612434B2

(12) United States Patent
Malvankar et al.

(10) Patent No.: US 12,612,434 B2
(45) Date of Patent: Apr. 28, 2026

(54) SYSTEMS AND METHODS FOR FORMING BIOLOGICAL NANOWIRES AND APPLICATIONS THEREOF

(71) Applicant: Yale University, New Haven, CT (US)

(72) Inventors: Nikhil Malvankar, New Haven, CT (US); Sibel Ebru Yalcin, Milford, CT (US)

(73) Assignee: Yale University, New Haven, CT (US)

( * ) Notice: Subject to any disclaimer, the term of this patent is extended or adjusted under 35 U.S.C. 154(b) by 1344 days.

(21) Appl. No.: 16/976,971

(22) PCT Filed: Mar. 1, 2019

(86) PCT No.: PCT/US2019/020403
§ 371 (c)(1),
(2) Date: Aug. 31, 2020

(87) PCT Pub. No.: WO2019/169331
PCT Pub. Date: Sep. 6, 2019

(65) Prior Publication Data
US 2021/0002332 A1 Jan. 7, 2021

Related U.S. Application Data

(60) Provisional application No. 62/775,236, filed on Dec. 4, 2018, provisional application No. 62/637,853, filed on Mar. 2, 2018.

(51) Int. Cl.
| | | |
|---|---|---|
| *C07K 14/195* | (2006.01) | |
| *C07K 14/80* | (2006.01) | |
| *C12P 21/02* | (2006.01) | |
| *H01B 1/12* | (2006.01) | |

(52) U.S. Cl.
CPC ............ *C07K 14/195* (2013.01); *C07K 14/80* (2013.01); *C12P 21/02* (2013.01); *H01B 1/12* (2013.01)

(58) Field of Classification Search
CPC ......... C07K 14/195; C07K 14/80; H01B 1/12
See application file for complete search history.

(56) References Cited

U.S. PATENT DOCUMENTS

2014/0239237 A1* 8/2014 Reguera ................... H01B 1/12
252/514

FOREIGN PATENT DOCUMENTS

WO    WO 2017/015306 A2    1/2017

OTHER PUBLICATIONS

Reardon et al. 2013 (Structure of the Type IV a Major Pilin form the Electrically Conductive Bacterial Nanowires of Geobacter sulfurreducens; Journal of Biological Chemistry 288(41): 29260-29266). (Year: 2013).*
Malvankar et al. 2012 (Lack of cytochrome involvement in long-range electron transport through conductive biofilms and nanowires of Geobacter sulfurreducens; Energy Environ Sci 5: 8651). (Year: 2012).*
Leang et al. 2010 (Alignment of the c-type cytochrome OmcS along Pili of Geobacter sulfurreducens; Applied and Environmental Microbiology 76(12): 4080-4084). (Year: 2010).*
Baquero et al. 2023 (Extracellular cytochrome nanowires appear to be ubiquitous in prokaryotes; Cell 186: 2853-2864). (Year: 2023).*
International Search Report and Written Opinion for International Application No. PCT/US2019/020403, mailed May 8, 2019.
International Preliminary Report on Patentability for International Application No. PCT/US2019/020403, mailed Sep. 17, 2020.
Adhikari et al., Conductivity of individual Geobacter pili. RSC Advances. Jan. 2016;6(10):8354-7.
Ashkenazy et al., ConSurf 2016: an improved methodology to estimate and visualize evolutionary conservation in macromolecules. Nucleic Acids Research. Jul. 8, 2016;44(W1):W344-50.
Beaussart et al., Quantifying the forces guiding microbial cell adhesion using single-cell force spectroscopy. Nature Protocols. May 2014;9(5):1049.
Bertini et al., Cytochrome c: occurrence and functions. Chemical Reviews. Jan. 11, 2006:106(1):90-115.
Boesen et al., Molecular dissection of bacterial nanowires. MBio. Jul. 1, 2013;4(3):e00270-13.
Cheung et al., A method to achieve homogeneous dispersion of large transmembrane complexes within the holes of carbon films for electron cryomicroscopy. Journal of Structural Biology. Apr. 1, 2013;182(1):51-6.
Childers et al., Geobacter metallireducens accesses insoluble Fe (III) oxide by chemotaxis. Nature. Apr. 2002;416(6882):767-9.
Clarke et al., Structure of a bacterial cell surface decaheme electron conduit. Proceedings of the National Academy of Sciences. Jun. 7, 2011;108(23):9384-9.
Cologgi et al., Extracellular reduction of uranium via Geobacter conductive pili as a protective cellular mechanism. Proceedings of the National Academy of Sciences. Sep. 13, 2011;108(37):15248-52.
Duvillaret et al., A reliable method for extraction of material parameters in terahertz time-domain spectroscopy. IEEE Journal of Selected Topics in Quantum Electronics. Sep. 1996;2(3):739-46.
Edwards et al., Electron transfer and electronic conduction through an intervening medium. Angewandte Chemie International Edition. Aug. 25, 2008;47(36):6758-65.

(Continued)

*Primary Examiner* — Mary Maille Lyons
(74) *Attorney, Agent, or Firm* — Wolf, Greenfield & Sacks, P.C.

(57) ABSTRACT

A nanowire may be isolated from a bacterium, wherein the nanowire includes c-type heme subunits or pili proteins and is capable of establishing an electrical connection with an insoluble electron acceptor. The c-type heme subunits may comprise OmcS or OmcZ cytochrome subunits or any combination thereof. The pili proteins may have an amino acid sequence with at least one residue modified, from a wild-type strain of the microorganism, to include an aromatic amino acid. The nanowire may have metallic or semiconducting conductive properties, and may be integrated into an electronic device.

18 Claims, 10 Drawing Sheets

Specification includes a Sequence Listing.

(56) References Cited

OTHER PUBLICATIONS

Egelman, A robust algorithm for the reconstruction of helical filaments using single-particle methods. Ultramicroscopy. Dec. 1, 2000;85(4):225-34.

Emsley et al., Coot: model-building tools for molecular graphics. Acta Crystallographica Section D: Biological Crystallography. Dec. 1, 2004;60(12):2126-32.

Endres et al., Colloquium: The quest for high-conductance DNA. Reviews of Modern Physics. Jan. 12, 2004;76(1):195.

Filman et al., Structure of a cytochrome-based bacterial nanowire. bioRxiv. Jan. 1, 2018:492645.

Hager et al., Type IV pili-mediated secretion modulates Francisella virulence. Molecular Microbiology. Oct. 2006;62(1):227-37.

Haldar et al., Conversion of amyloid fibrils of cytochrome c to mature nanorods through a honeycomb morphology. Langmuir. Apr. 14, 2015;31(14):4213-23.

He et al., Length dependence of charge transport in oligoanilines. Applied physics letters. Feb. 12, 2007;90(7):072112.

Heeger et al., Solitons in conducting polymers. Reviews of Modern Physics. Jul. 1, 1988;60(3):781.

Hirota et al., Cytochrome c polymerization by successive domain swapping at the C-terminal helix. Proceedings of the National Academy of Sciences. Jul. 20, 2010;107(29):12854-9.

Holmes et al., Microarray and genetic analysis of electron transfer to electrodes in Geobacter sulfurreducens. Environmental Microbiology. Oct. 2006;8(10):1805-15.

Hong-Geller et al., Small molecule screens to identify inhibitors of infectious disease. Chapter 5 of Drug Discovery: InTech, ed. E. Shelmy Hany El. Jan. 23, 2013:157-75.

Ing et al., Geobacter sulfurreducens pili support ohmic electronic conduction in aqueous solution. Physical Chemistry Chemical Physics. Aug. 16, 2017;19(32):21791-9.

Janiak, A critical account on π-π stacking in metal complexes with aromatic nitrogen-containing ligands. Journal of the Chemical Society, Dalton Transactions. Sep. 2000 Sep:3885-96.

Jiang et al., Cysteine linkages accelerate electron flow through tetra-heme protein STC. Journal of the American Chemical Society. Dec. 6, 2017:139(48):17237-40.

Kilmury et al., Type IV pilins regulate their own expression via direct intramembrane interactions with the sensor kinase PilS. Proceedings of the National Academy of Sciences. May 24, 2016;113(21):6017-22.

Klimes et al., Production of pilus-like filaments in Geobacter sulfurreducens in the absence of the type IV pilin protein PilA. FEMS microbiology letters. Sep. 1, 2010;310(1):62-8.

Leang et al., Alignment of the c-type cytochrome OmcS along pili of Geobacter sulfurreducens. Applied and Environmental Microbiology. Jun. 15, 2010;76(12):4080-4.

Lebedev et al., On the electron transfer through Geobacter sulfurreducens P il A protein. Journal of Polymer Science Part B: Polymer Physics. Dec. 15, 2015;53(24):1706-17.

Li et al., Electron counting and beam-induced motion correction enable near-atomic-resolution single-particle cryo-EM. Nature Methods. Jun. 2013;10(6):584-90.

Liu et al., Syntrophic growth with direct interspecies electron transfer between pili-free *Geobacter* species. The ISME Journal. Sep. 2018;12(9):2142-51.

Livshits et al., Long-range charge transport in single G-quadruplex DNA molecules. Nature nanotechnology. Dec. 2014;9(12):1040-6.

Malvankar et al., Electronic conductivity in living biofilms: physical meaning, mechanisms, and measurement methods. Chapter 7 of Biofilms in Bioelectrochemical Systems. Edited by Beyenal H, Babauta JT. Wiley. Sep. 8, 2015:211-47.

Malvankar et al., Microbial nanowires for bioenergy applications. Current Opinion in Biotechnology. Jun. 1, 2014;27:88-95.

Malvankar et al., Structural basis for metallic-like conductivity in microbial nanowires. MBio. Mar. 2015;6(2):e00084-15.

Malvankar et al., Tunable metallic-like conductivity in microbial nanowire networks. Nature nanotechnology. Sep. 2011;6(9):573-9.

Malvankar et al., Visualization of charge propagation along individual pili proteins using ambient electrostatic force microscopy. Nature nanotechnology. Dec. 2014;9(12):1012-7.

Margoliash et al., Interconversion of horse heart cytochrome c monomer and polymers. Journal of Biological Chemistry. Nov. 1, 1962;237(11):3397-405.

Marsili et al., Shewanella secretes flavins that mediate extracellular electron transfer. Proceedings of the National Academy of Sciences. Mar. 11, 2008;105(10):3968-73.

Mehta et al., Outer membrane c-type cytochromes required for Fe (III) and Mn (IV) oxide reduction in Geobacter sulfurreducens. Applied and environmental microbiology. Dec. 1, 2005;71(12):8634-41.

Mélin et al., Electrostatic force microscopy and Kelvin force microscopy as a probe of the electrostatic and electronic properties of carbon nanotubes. Chapter 4 of Scanning Probe Microscopy in Nanoscience and Nanotechnology. 2010:89-128.

Mindell et al., Accurate determination of local defocus and specimen tilt in electron microscopy. Journal of Structural Biology. Jun. 1, 2003;142(3):334-47.

Morita et al., Potential for direct interspecies electron transfer in methanogenic wastewater digester aggregates. MBio. Jul. 2011;2(4)e00159-11.

Neu et al., Exploring the solid state phase transition in dl-norvaline with terahertz spectroscopy. Physical Chemistry Chemical Physics. Nov. 2018;20(1):276-83.

Neumann et al., Validating resolution revolution. Structure. May 1, 2018;26(5):785-95.

O'Brien et al., A Simple and Low-Cost Procedure for Growing Geobacter sulfurreducens Cell Cultures and Biofilms in Bioelectrochemical Systems. Current Protocols in Microbiology. Nov. 2016;43(1):A.4K.1-A.4K.27.

Park et al., Homologous overexpression of omcZ, a gene for an outer surface c-type cytochrome of Geobacter sulfurreducens by single-step gene replacement. Biotechnology Letters. Oct. 2011;33(10):2043-8.

Pettersen et al., UCSF Chimera—a visualization system for exploratory research and analysis. Journal of Computational Chemistry. Oct. 2004;25(13):1605-12.

Potra et al., Interior-point methods. Journal of Computational and Applied Mathematics. Dec. 1, 2000;124(1-2):281-302.

Priyadarshy et al., DNA is not a molecular wire: protein-like electron-transfer predicted for an extended π-electron system. The Journal of Physical Chemistry. Oct. 31, 1996;100(44):17678-82.

Qian et al., Biochemical characterization of purified OmcS, a c-type cytochrome required for insoluble Fe (III) reduction in Geobacter sulfurreducens. Biochimica et Biophysica Acta (BBA)—Bioenergetics. Apr. 1, 2011;1807(4):404-12.

Quinn et al., Biogeochemical forces shape the composition and physiology of polymicrobial communities in the cystic fibrosis lung. MBio. May 18, 2014;5(2):e00956-13.

Reardon et al., Structure of the type IVa major pilin from the electrically conductive bacterial nanowires of Geobacter sulfurreducens. Journal of Biological Chemistry. Oct. 11, 2013;288(41):29260-6.

Reguera et al., Extracellular electron transfer via microbial nanowires. Nature. Jun. 23, 2005;435(7045):1098-101.

Richter et al., Two isoforms of Geobacter sulfurreducens PilA have distinct roles in pilus biogenesis, cytochrome localization, extracellular electron transfer, and biofilm formation. Journal of bacteriology. May 15, 2012;194(10):2551-63.

Rotaru et al., A new model for electron flow during anaerobic digestion: direct interspecies electron transfer to Methanosaeta for the reduction of carbon dioxide to methane. Energy & Environmental Science. Oct. 2014;7(1):408-15.

Scheres, Relion: implementation of a Bayesian approach to cryo-EM structure determination. Journal of structural biology. Dec. 1, 2012;180(3):519-30.

Shinwari et al., Electrical conductance in biological molecules. Advanced Functional Materials. Jun. 23, 2010;20(12):1865-83.

Shrestha et al., Correlation between microbial community and granule conductivity in anaerobic bioreactors for brewery wastewater treatment. Bioresource Technology. Dec. 1, 2014;174:306-10.

(56) References Cited

OTHER PUBLICATIONS

Steidl et al., Mechanistic stratification in electroactive biofilms of Geobacter sulfurreducens mediated by pilus nanowires. Nature communications. Aug. 2, 2016;7(1):1-11.

Subramaniam et al., Resolution advances in cryo-EM enable application to drug discovery. Current Opinion in Structural Biology. Dec. 1, 2016;41:194-202.

Summers et al., Direct exchange of electrons within aggregates of an evolved syntrophic coculture of anaerobic bacteria. Science. Dec. 3, 2010;330(6009):1413-5.

Tan et al., Expressing the Geobacter metallireducens PilA in Geobacter sulfurreducens yields pili with exceptional conductivity. MBio. Mar. 8, 2017;8(1):e02203-16.

Tan et al., Synthetic biological protein nanowires with high conductivity. Small. Sep. 2016;12(33):4481-5.

Tan et al., The low conductivity of Geobacter uraniireducens pili suggests a diversity of extracellular electron transfer mechanisms in the genus Geobacter. Frontiers in Microbiology. Jun. 28, 2016;7:980.

Tang et al., EMAN2: an extensible image processing suite for electron microscopy. Journal of Structural Biology. Jan. 1, 2007;157(1):38-46.

Ueki et al., Identification of multicomponent histidine-aspartate phosphorelay system controlling flagellar and motility gene expression in Geobacter species. Journal of Biological Chemistry. Mar. 30, 2012;287(14):10958-66.

Vargas et al., Aromatic amino acids required for pili conductivity and long-range extracellular electron transport in Geobacter sulfurreducens. MBio. May 1, 2013;4(2):e00105-13.

Wagner, Conductive consortia. Nature. Oct. 2015;526(7574):513-4.

Wang et al., Cryoelectron microscopy reconstructions of the Pseudomonas aeruginosa and Neisseria gonorrhoeae type IV pili at sub-nanometer resolution. Structure. Sep. 5, 2017;25(9):1423-35.

Wang et al., De novo protein structure determination from near-atomic-resolution cryo-EM maps. Nature Methods. Apr. 2015;12(4):335-8.

Wang et al., Structure of microbial nanowires reveals stacked hemes that transport electrons over micrometers. Cell. Apr. 4, 2019;177(2):361-9.

Williams et al., MolProbity: More and better reference data for improved all-atom structure validation. Protein Science. Jan. 2018;27(1):293-315.

Xiao et al., Low energy atomic models suggesting a pilus structure that could account for electrical conductivity of Geobacter sulfurreducens pili. Scientific reports. Mar. 22, 2016;6(1):1-9.

Yan et al., Inter-Aromatic Distances in Geobacter Sulfurreducens Pili Relevant to Biofilm Charge Transport. Advanced Materials. Mar. 2015;27(11):1908-11.

Zeglis et al., Metallo-intercalators and metallo-insertors. Chemical Communications. Nov. 2007(44):4565-79.

* cited by examiner

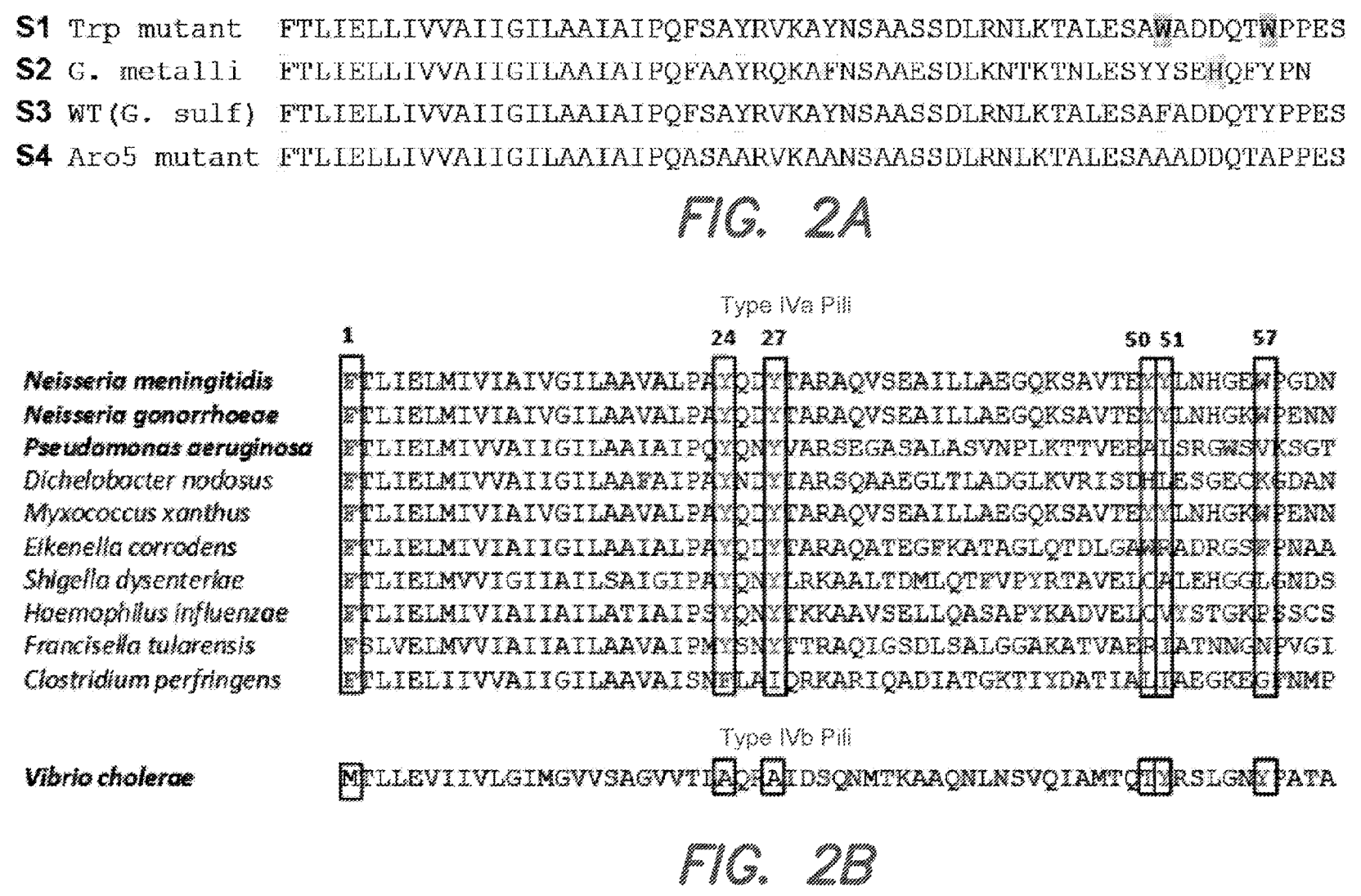

S1 Trp mutant   FTLIELLIVVAIIGILAAIAIPQFSAYRVKAYNSAASSDLRNLKTALESAWADDQTWPPES

S2 G. metalli   FTLIELLIVVAIIGILAAIAIPQFAAYRQKAPNSAAESDLKNTKTNLESYYSEHQFYPN

S3 WT(G. sulf)   FTLIELLIVVAIIGILAAIAIPQFSAYRVKAYNSAASSDLRNLKTALESAFADDQTYPPES

S4 Aro5 mutant   FTLIELLIVVAIIGILAAIAIPQASAARVKAANSAASSDLRNLKTALESAAADDQTAPPES

*FIG. 2A*

Type IVa Pili

| | 1 | 24 27 | | 50 51 | 57 |
|---|---|---|---|---|---|
| *Neisseria meningitidis* | FTLIELMIVIAIVGILAAVALPAYQ | ARAQVSEAILLAEGQKSAVTE | LNHGEM | GDN |
| *Neisseria gonorrhoeae* | FTLIELMIVIAIVGILAAVALPAYQ | ARAQVSEAILLAEGQKSAVTE | LNHGKM | PENN |
| *Pseudomonas aeruginosa* | FTLIELMIVVAIIGILAAIAIPQYQ | VARSEGASALASVNPLKTTVEE | SRGWSV | SGT |
| *Dichelobacter nodosus* | FTLIELMIVVAIIGILAAIAIPNYQ | ARSQAAEGLTIADGLKVRISM | ESGEQK | DAN |
| *Myxococcus xanthus* | FTLIELMIVIAIVGILAAVALPNYQ | ARAQVSEAILLAEGQKSAVTE | LNHGKM | PENN |
| *Eikenella corrodens* | FTLIELMIVIAIIGILAAIALPNYQ | ARAQATEGFKATAGLQTDLGK | ADRGS | NAA |
| *Shigella dysenteriae* | FTLIELMVVIGIIATLSAIGIPAYQ | RKAALTDMLQTFVPYRTAVEIQ | LEHGGL | NDS |
| *Haemophilus influenzae* | FTLIELMIVIAIIATIAATIAIPSYQ | KKAAVSELLQASAPYKADVEIQ | STGKP | SCS |
| *Francisella tularensis* | FDLVELMIVVAIIAILAAVAIPMYS | TRAQIGSDLSALGGAKATVAEP | ATNMGM | PVGI |
| *Clostridium perfringens* | FTLIELLIVVALIGIILAAVAISML | ORKARIQADIATGKTIYDATIA | AEGKFG | NMP |

*FIG. 2B*

Type IVb Pili

| | 1 | | | | |
|---|---|---|---|---|---|
| *Vibrio cholerae* | MTLLEVIIVLGIMGVVSAGVVTA | D | DSQNMTKAAQWLNSVQIAMTQ | RSIGK | ATA |

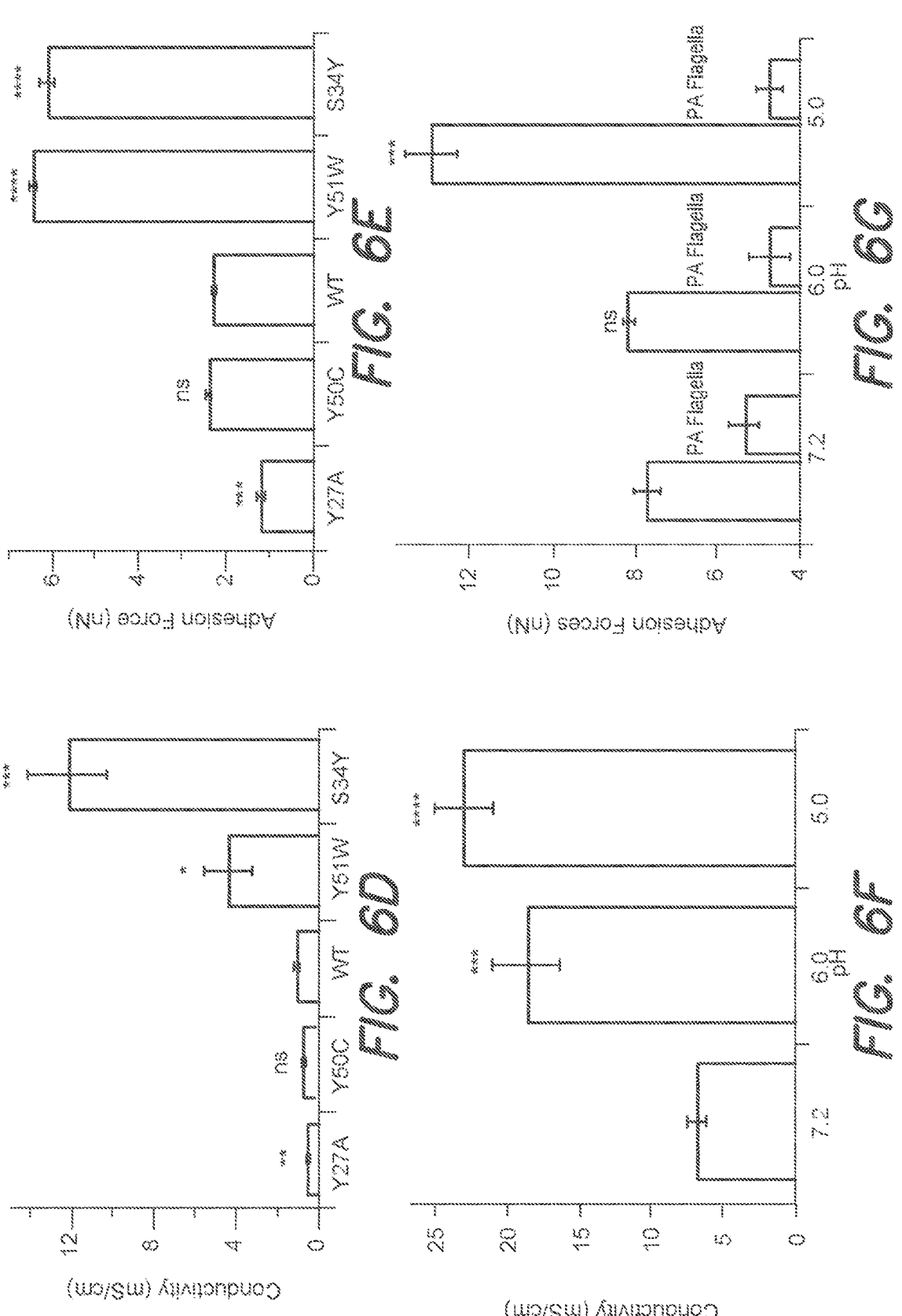

SEQUENCE LISTING

```
<160> NUMBER OF SEQ ID NOS: 15

<210> SEQ ID NO 1
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 1

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Trp Ala Asp Asp Gln Thr Trp Pro Pro Glu Ser
    50                  55                  60

<210> SEQ ID NO 2
<211> LENGTH: 59
<212> TYPE: PRT
<213> ORGANISM: Geobacter metallireducens

<400> SEQUENCE: 2

Phe Thr Leu Ile Glu Leu Leu Ile Val Val Ala Ile Ile Gly Ile Leu
1               5                   10                  15

Ala Ala Ile Ala Ile Pro Gln Phe Ala Ala Tyr Arg Gln Lys Ala Phe
            20                  25                  30

Asn Ser Ala Ala Glu Ser Asp Leu Lys Asn Thr Lys Thr Asn Leu Glu
        35                  40                  45

Ser Tyr Tyr Ser Glu His Gln Phe Tyr Pro Asn
    50                  55

<210> SEQ ID NO 3
<211> LENGTH: 61
<212> TYPE: PRT
<213> ORGANISM: Geobacter sulfurreducens

<400> SEQUENCE: 3
```

-continued

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60

<210> SEQ ID NO 4
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 4

Phe Thr Leu Ile Glu Leu Leu Ile Val Val Ala Ile Ile Gly Ile Leu
1               5                   10                  15

Ala Ala Ile Ala Ile Pro Gln Ala Ser Ala Ala Arg Val Lys Ala Ala
            20                  25                  30

Asn Ser Ala Ala Ser Ser Asp Leu Arg Asn Leu Lys Thr Ala Leu Glu
        35                  40                  45

Ser Ala Ala Ala Asp Asp Gln Thr Ala Pro Pro Glu Ser
    50                  55                  60

<210> SEQ ID NO 5
<211> LENGTH: 61
<212> TYPE: PRT
<213> ORGANISM: Neisseria meningitidis

<400> SEQUENCE: 5

Phe Thr Leu Ile Glu Leu Met Ile Val Ile Ala Ile Val Gly Ile Leu
1               5                   10                  15

Ala Ala Val Ala Leu Pro Ala Tyr Gln Asp Tyr Thr Ala Arg Ala Gln
            20                  25                  30

Val Ser Glu Ala Ile Leu Leu Ala Glu Gly Gln Lys Ser Ala Val Thr
        35                  40                  45

Glu Tyr Tyr Leu Asn His Gly Glu Trp Pro Gly Asp Asn
    50                  55                  60

<210> SEQ ID NO 6
<211> LENGTH: 61
<212> TYPE: PRT
<213> ORGANISM: Neisseria gonorrhoeae

<400> SEQUENCE: 6

Phe Thr Leu Ile Glu Leu Met Ile Val Ile Ala Ile Val Gly Ile Leu
1               5                   10                  15

Ala Ala Val Ala Leu Pro Ala Tyr Gln Asp Tyr Thr Ala Arg Ala Gln
            20                  25                  30

Val Ser Glu Ala Ile Leu Leu Ala Glu Gly Gln Lys Ser Ala Val Thr
        35                  40                  45

Glu Tyr Tyr Leu Asn His Gly Lys Trp Pro Glu Asn Asn
    50                  55                  60

<210> SEQ ID NO 7
<211> LENGTH: 61
<212> TYPE: PRT
<213> ORGANISM: Pseudomonas aeruginosa
```

-continued

<400> SEQUENCE: 7

```
Phe Thr Leu Ile Glu Leu Met Ile Val Val Ala Ile Ile Gly Ile Leu
1               5                   10                  15

Ala Ala Ile Ala Ile Pro Gln Tyr Gln Asn Tyr Val Ala Arg Ser Glu
            20                  25                  30

Gly Ala Ser Ala Leu Ala Ser Val Asn Pro Leu Lys Thr Thr Val Glu
        35                  40                  45

Glu Ala Ile Ser Arg Gly Trp Ser Val Lys Ser Gly Thr
    50                  55                  60
```

<210> SEQ ID NO 8
<211> LENGTH: 61
<212> TYPE: PRT
<213> ORGANISM: Dichelobacter nodosus

<400> SEQUENCE: 8

```
Phe Thr Leu Ile Glu Leu Met Ile Val Val Ala Ile Ile Gly Ile Leu
1               5                   10                  15

Ala Ala Phe Ala Ile Pro Ala Tyr Asn Asp Tyr Ile Ala Arg Ser Gln
            20                  25                  30

Ala Ala Glu Gly Leu Thr Leu Ala Asp Gly Leu Lys Val Arg Ile Ser
        35                  40                  45

Asp His Leu Glu Ser Gly Glu Cys Lys Gly Asp Ala Asn
    50                  55                  60
```

<210> SEQ ID NO 9
<211> LENGTH: 61
<212> TYPE: PRT
<213> ORGANISM: Myxococcus xanthus

<400> SEQUENCE: 9

```
Phe Thr Leu Ile Glu Leu Met Ile Val Ile Ala Ile Val Gly Ile Leu
1               5                   10                  15

Ala Ala Val Ala Leu Pro Ala Tyr Gln Asp Tyr Thr Ala Arg Ala Gln
            20                  25                  30

Val Ser Glu Ala Ile Leu Leu Ala Glu Gly Gln Lys Ser Ala Val Thr
        35                  40                  45

Glu Tyr Tyr Leu Asn His Gly Lys Trp Pro Glu Asn Asn
    50                  55                  60
```

<210> SEQ ID NO 10
<211> LENGTH: 61
<212> TYPE: PRT
<213> ORGANISM: Eikenella corrodens

<400> SEQUENCE: 10

```
Phe Thr Leu Ile Glu Leu Met Ile Val Ile Ala Ile Ile Gly Ile Leu
1               5                   10                  15

Ala Ala Ile Ala Leu Pro Ala Tyr Gln Asp Tyr Thr Ala Arg Ala Gln
            20                  25                  30

Ala Thr Glu Gly Phe Lys Ala Thr Ala Gly Leu Gln Thr Asp Leu Gly
        35                  40                  45

Ala Trp Arg Ala Asp Arg Gly Ser Phe Pro Asn Ala Ala
    50                  55                  60
```

<210> SEQ ID NO 11
<211> LENGTH: 61
<212> TYPE: PRT

<213> ORGANISM: Shigella dysenteriae

<400> SEQUENCE: 11

Phe Thr Leu Ile Glu Leu Met Val Val Ile Gly Ile Ile Ala Ile Leu
1               5                   10                  15

Ser Ala Ile Gly Ile Pro Ala Tyr Gln Asn Tyr Leu Arg Lys Ala Ala
            20                  25                  30

Leu Thr Asp Met Leu Gln Thr Phe Val Pro Tyr Arg Thr Ala Val Glu
        35                  40                  45

Leu Cys Ala Leu Glu His Gly Gly Leu Gly Asn Asp Ser
    50                  55                  60

<210> SEQ ID NO 12
<211> LENGTH: 61
<212> TYPE: PRT
<213> ORGANISM: Haemophilus influenzae

<400> SEQUENCE: 12

Phe Thr Leu Ile Glu Leu Met Ile Val Ile Ala Ile Ile Ala Ile Leu
1               5                   10                  15

Ala Thr Ile Ala Ile Pro Ser Tyr Gln Asn Tyr Thr Lys Lys Ala Ala
            20                  25                  30

Val Ser Glu Leu Leu Gln Ala Ser Ala Pro Tyr Lys Ala Asp Val Glu
        35                  40                  45

Leu Cys Val Tyr Ser Thr Gly Lys Pro Ser Ser Cys Ser
    50                  55                  60

<210> SEQ ID NO 13
<211> LENGTH: 61
<212> TYPE: PRT
<213> ORGANISM: Francisella tularensis

<400> SEQUENCE: 13

Phe Ser Leu Val Glu Leu Met Val Val Ile Ala Ile Ile Ala Ile Leu
1               5                   10                  15

Ala Ala Val Ala Ile Pro Met Tyr Ser Asn Tyr Thr Thr Arg Ala Gln
            20                  25                  30

Ile Gly Ser Asp Leu Ser Ala Leu Gly Gly Ala Lys Ala Thr Val Ala
        35                  40                  45

Glu Arg Ile Ala Thr Asn Asn Gly Asn Pro Val Gly Ile
    50                  55                  60

<210> SEQ ID NO 14
<211> LENGTH: 61
<212> TYPE: PRT
<213> ORGANISM: Clostridium perfringens

<400> SEQUENCE: 14

Phe Thr Leu Ile Glu Leu Ile Ile Val Val Ala Ile Ile Gly Ile Leu
1               5                   10                  15

Ala Ala Val Ala Ile Ser Asn Phe Leu Ala Ile Gln Arg Lys Ala Arg
            20                  25                  30

Ile Gln Ala Asp Ile Ala Thr Gly Lys Thr Ile Tyr Asp Ala Thr Ile
        35                  40                  45

Ala Leu Ile Ala Glu Gly Lys Glu Gly Phe Asn Met Pro
    50                  55                  60

<210> SEQ ID NO 15
<211> LENGTH: 61

-continued

```
<212> TYPE: PRT
<213> ORGANISM: Vibrio cholerae

<400> SEQUENCE: 15

Met Thr Leu Leu Glu Val Ile Ile Val Leu Gly Ile Met Gly Val Val
1               5                   10                  15

Ser Ala Gly Val Val Thr Leu Ala Gln Arg Ala Ile Asp Ser Gln Asn
            20                  25                  30

Met Thr Lys Ala Ala Gln Asn Leu Asn Ser Val Gln Ile Ala Met Thr
        35                  40                  45

Gln Thr Tyr Arg Ser Leu Gly Asn Tyr Pro Ala Thr Ala
    50                  55                  60
```

SYSTEMS AND METHODS FOR FORMING BIOLOGICAL NANOWIRES AND APPLICATIONS THEREOF

CROSS-REFERENCE TO RELATED APPLICATIONS

The present application is a national stage filing under 35 U.S.C. 371 of International Patent Application Serial No. PCT/US2019/020403, filed Mar. 1, 2019, titled "SYSTEMS AND METHODS FOR FORMING BIOLOGICAL NANOWIRES AND APPLICATIONS THEREOF," which is hereby incorporated by reference in its entirety. The present application claims the benefit under 35 U.S.C. § 119(e) of U.S. Provisional Patent Application No. 62/637, 853, filed Mar. 2, 2018, titled "SYSTEMS AND METHODS FOR FORMING ELECTRONIC BIOMATERIALS AND DEVICES HAVING ELECTRONIC BIOMATERIALS," which is hereby incorporated by reference in its entirety. The present application claims the benefit under 35 U.S.C. § 119(e) of U.S. Provisional Patent Application No. 62/775, 236, filed Dec. 4, 2018, titled "GEOBACTER PROTEIN NANOWIRES," which is hereby incorporated by reference in its entirety.

GOVERNMENT FUNDING

This invention was made with government support under AI138259 awarded by the National Institutes of Health, under 1749662 awarded by the National Science Foundation, and under W911NF-18-2-0100 awarded by the Defense Advanced Research Project Agency Army Research Office. The government has certain rights in the invention.

BACKGROUND

Conventional electronic nanowires typically comprise inorganic materials and may exhibit a range of electronic behaviors from superconducting to insulating. However, conventional electronic nanowires may be difficult to manufacture and may be toxic, which may hinder their biocompatibility. Synthetic conducting polymers are typically stiff and brittle, as well as non-biodegradable, which may hinder their efficient interfacing with living tissues.

SUMMARY

Biologically produced electronic nanomaterials may be able to bidirectionally interface between silicon-based electronic systems and biological systems. Biological nanomaterials are relatively inexpensive to manufacture and can be mass produced in environmentally friendly manner. They may possess new features such as stretchability, non-toxicity, controlled biological properties, and mixed electronic and ionic conductivity. These materials will enable novel applications in fields including but not limited to imaging, robotics, sensors, and cellular signaling.

Conducting, protein-based nanowires represent a new class of bioelectronic materials. Certain soil bacteria and pathogens can transfer electrons using protein nanowires, altering their charge environment and enabling functions such as extracellular respiration and adhesion within a biofilm. Methanogenic, methane- and hydrocarbon-oxidizing microbes have been also shown to transfer electrons via protein nanowires for syntrophic growth in diverse environments. A non-limiting selection of such bacteria includes *Geobacter sulfurreducens, Pseudomonas aeruginosa, Neis-*

*seria gonorrhoeae, Neisseria meningidis* and *Escherichia coli*. Culturing these bacteria under conditions that encourage nanowire growth may be a cost-effective way to produce electronic nanowires. Synthetic biological techniques may also enable the engineering of protein nanowires with tunable electronic properties.

Some embodiments relate to a nanowire isolated from a bacterium, the nanowire comprising c-type heme subunits or pili proteins capable of establishing an electrical connection with an insoluble electron acceptor. The c-type heme subunits may comprise OmcS or OmcZ cytochrome subunits or any combination thereof. The pili proteins may have an amino acid sequence with at least one residue modified, from a wild-type strain of the microorganism, to include an aromatic amino acid. The nanowire may have metallic or semiconducting conductive properties.

Some embodiments relate to a method of synthesizing any one of the above described nanowires. The method may comprise culturing a bacterium configured to express a nanowire in a cell culture medium comprising an electron acceptor, wherein the electron acceptor may be an electrode. In some embodiments, the method comprises isolating the nanowire from the bacterium.

Some embodiments relate to a method of synthesizing a cytochrome nanowire using a bacterium from the family Geobacteraceae. The method may comprise culturing a bacterium from the family Geobacteraceae configured to express a cytochrome nanowire in a cell culture medium comprising an electron acceptor, wherein the electron acceptor may be an electrode. In some embodiments, the method comprises isolating the cytochrome nanowire from the bacterium.

Some embodiments relate to an electronic device comprising any of the above described nanowires. The electronic device may comprise at least one electrode. The at least one electrode may be electrically coupled to the any of the above described nanowires.

The foregoing apparatus and method embodiments may be implemented with any suitable combination of aspects, features, and acts described above or in further detail below. These and other aspects, embodiments, and features of the present application can be more fully understood from the following description in conjunction with the accompanying drawings.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 2A illustrates a subset of sequences of *Geobacter* strains. Sequences correspond from top to bottom to SEQ ID NOs: 1-4;

FIG. 2B illustrates a subset of sequences of bacteria which produce Type IV pili. Sequences correspond from top to bottom to SEQ ID NOs: 5-15;

FIG. 6D illustrates conductivity measurements of protein nanowires from various strains of *N. meningitidis;*

FIG. 6E illustrates adhesion force measurements of protein nanowires from various strains of *N. meningitidis;*

FIG. 6F illustrates conductivity measurements of protein nanowires from *P. aeruginosa* under decreasing pH conditions;

FIG. 6G illustrates adhesion force measurements of protein nanowires and flagella from *P. aeruginosa* under decreasing pH conditions;

DETAILED DESCRIPTION

Figures 1A, 1B, 1C:
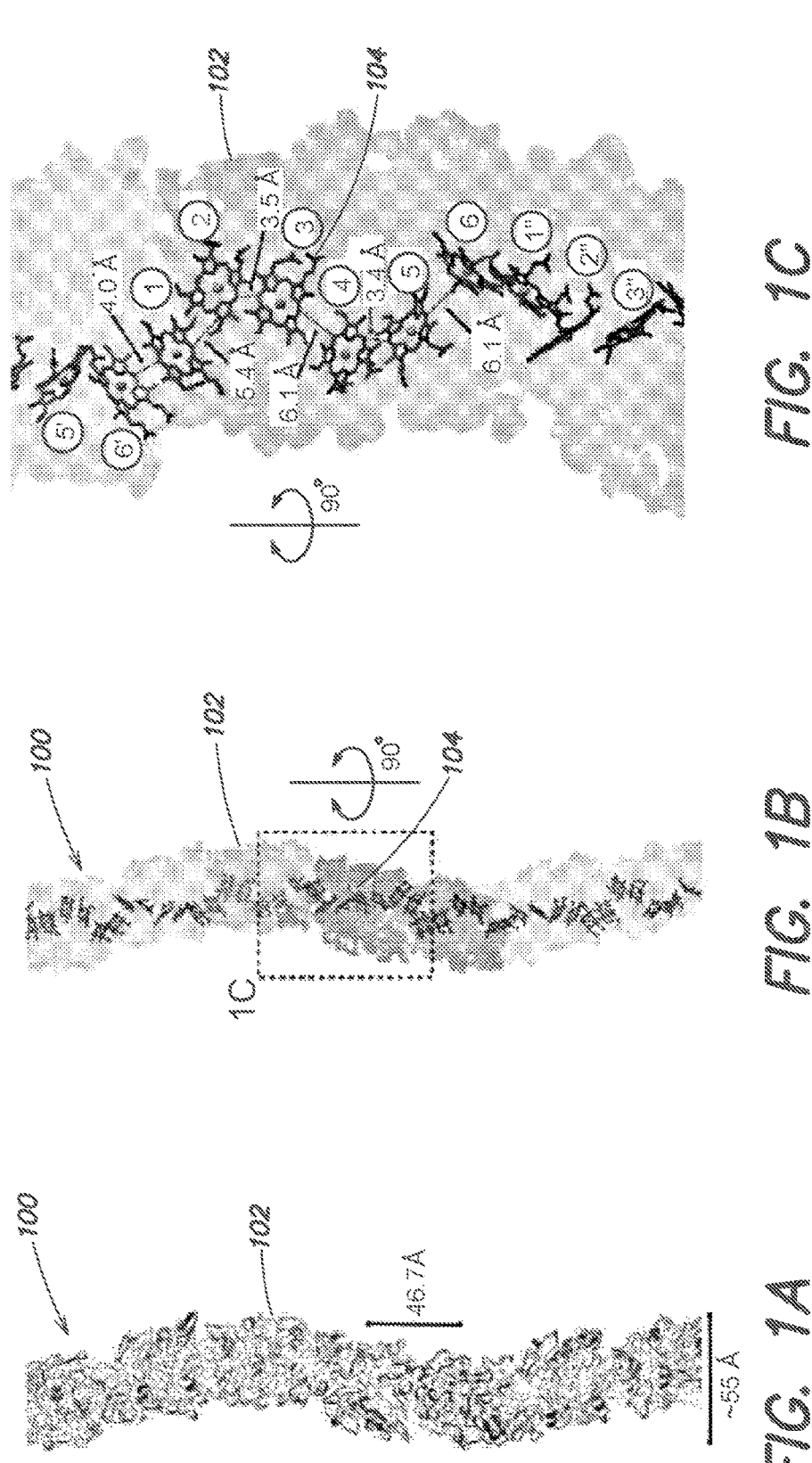
FIG. 1A illustrates a surface of a nanowire comprising OmcS subunits.
FIG. 1B illustrates a chain of heme molecules in a nanowire comprising OmcS subunits.
FIG. 1C illustrates a molecular-level zoomed view of the arrangement of OmcS heme molecules in a nanowire.

Aspects of the present technology relate to techniques for forming nanowires with desired conductive properties. The nanowires described herein include cytochrome and pili nanowires produced by bacteria under particular conditions. The inventors have recognized and appreciated that the conductivity of cytochrome nanowires depends on the protein structure of the cytochrome nanowires, including the type and arrangement of heme subunits within the protein structure. In particular, the inventors have recognized and appreciated that the conductivity of cytochrome nanowires depends on the ability of heme subunits to polymerize such that the heme subunits may transfer electrons over a distance. The inventors have recognized and appreciated that c-type cytochromes OmcS and OmcZ are particularly suitable for forming conductive cytochrome nanowires. Accordingly, embodiments of the present technology involve techniques for forming nanowires by growing a bacterium under one or more conditions that induce cytochrome and/or pili nanowire production by the bacterium.

The inventors have recognized and appreciated that the expression of cytochrome nanowires by a bacterium occurs in tandem with the expression of pilin proteins such as pilA, pilE, or fimA. In particular, the inventors have recognized and appreciated that expression of cytochrome nanowires by a bacterium can be different between strains of the bacteria (e.g. amount or types of cytochromes which are expressed by the bacterium). For example, an additional strain may include different amino acids for one or more residues of an amino acid sequence corresponding to pili protein. If an overexpression of cytochrome nanowires is desired, then the strain may include an aromatic amino acid (e.g., trypotophan) at the one or more residues, which may lead to increased expression of cytochrome nanowires. Nanowires formed using these techniques may include nanowires having insulating, semiconducting, or metallic properties. In some embodiments, the conductivity of the nanowire increases by 1000-fold when lowering the pH and by 10,000-fold by lowering the temperature, surpassing the conductivity of copper. Under these conditions, the nanowire may be used to develop pH and temperature sensors as well as to develop materials that function under extreme conditions such as very low (<10 K) or high (>100° C.) temperatures and acidic/aqueous conditions.

The nanowires described herein may have suitable properties for implementation in an electronic device. Such properties include a nanowire having substantially few defects and/or impurities that may impact conductivity of the nanowire. These properties include flexibility of the nanowire, ease of production, low cost of production, and small or no toxicity. In contrast, synthetic conducting polymers are typically stiff and brittle, as well as non-biodegradable, which can reduce their applications in certain types of devices, such in applications that involve interfacing with living tissues. In contrast to synthetic materials, which may involve the use of toxic chemicals and high temperatures for production, these nanowires are less expensive and can be mass produced in a more environmentally friendly manner. Examples of electronic devices that may implement the nanowires described herein include imaging devices, robotics devices, biosensors, and medical devices.

To measure and assess the conductivity of nanowires, the inventors have recognized and appreciated that techniques typically used in measuring conductivity of synthetic polymers can lead to inaccurate results when used to measure conductivity of biological nanowires, including nanowires comprising proteins. Accordingly, embodiments of the present technology relate to systems and methods for performing and analyzing measurements to assess conductivity of a material, and are particular suitable for determining conductivity of nanowires. These techniques may involve performing conductivity measurements on the nanowire while the nanowire remains in an aqueous environment. Some embodiments involve systems and methods for measuring electrical conductivity by using four electrodes and applying a range of currents to two outer electrodes and measuring voltages between the two inner electrodes. Such systems and methods may include separating contact resistance, ion conductivity and measuring electron conductivity. Voltages measured between the inner electrodes that exhibit linear behavior may provide an indication of electrical conductivity of a material positioned on the electrodes.

The inventors have further recognized and appreciated that the conductive nature of nanowires can impact how bacteria attach to surfaces, including adhesion to other microorganisms or host surfaces that cause bacterial infections. For example, the nanowires of pathogenic bacteria, such as *Pseudomonas aeruginosa, Neisseria gonorrhoeae,* and *Neisseria meningitidis,* are also electrically conductive, which is important for their adhesion. The systems and methods for measuring conductivity of nanowires described in the present technology may be used to assess adhesion of microorganisms, which may allow for evaluation of techniques that target disrupting microbial adhesion to surfaces. Accordingly, these techniques for measuring conductivity of nanowires may allow for evaluation of anti-microbial therapies, drug development to suppress bacterial infections, and biofouling prevention techniques.

Following below are more detailed descriptions of various concepts related to, and embodiments of, techniques for the manufacture of cytochrome nanowires and electronic devices comprising cytochrome nanowires. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

Aspects of the present technology relate to cytochrome nanowires which are expression products of a bacterium. FIGS. 1A-C illustrate an atomic structure of the protein nanowire and polymerized arrangement of hemes which form the structure of a cytochrome nanowire. In particular, the illustrated nanowire in FIGS. 1A-C comprises OmcS subunits, a c-type cytochrome, and is reconstructed from protein nanowires isolated from the wild type (WT) strain of *Geobacter sulfurreducens*. FIG. 1A depicts a surface of a reconstruction 100 with superimposed ribbon models of the OmcS subunits 102 with three subunits 102 in the center. Protein nanowires 100 purified from the WT strain showed a sinusoidal morphology with a period of ~200 Å with ~4.3 subunits 102 per turn of a 1-start helix. The 1-start nanowire helix is left-handed, with a rise per subunit of 46.7 Å and a rotation of −83.1°, substantially different than type IV pili that typically show a rise of ~10 Å and a right-handed helix.

As seen in FIGS. 1B and 1C, each subunit 102 contains six hemes 104 closely stacked over the micrometer-lengths of the nanowires. FIG. 1C depicts a single OmcS subunit 102 from the zoomed region of the box shown in FIG. 1B with the minimum observed edge-to-edge distances indicated between hemes numbered in circles. The distance between two hemes 104 in adjacent subunits (heme 1 and heme 6') is comparable to the distances between parallel stacked hemes 104 within a subunit (heme 2:heme 3 and heme 4:heme 5).

The inventors have appreciated and recognized that while cytochromes can polymerize in ethanolic solutions and structures have been determined for aggregates up to tetramers, natural polymerization of the type described herein has not been previously known. As shown in FIG. 1C, hemes in the OmcS nanowires form parallel-stacked pairs, with each pair perpendicular to the next, forming a continuous chain over the entire length of the nanowire. The minimum edge-to-edge distances between the parallel hemes is 3.4 to 4.1 Å, and 5.4 to 6.1 Å between the perpendicular stacked pairs.

As discussed previously, the expression of cytochrome nanowires to the outer surface of a bacterium occurs with the expression of pilin proteins (e.g. pilA for *G. sulfurreducens*). Strains of bacteria with alterations made to one or more residues of an amino acid sequence corresponding to pilA protein may express different types or amounts of cytochrome nanowires. FIG. 2A shows sequences for several mutant strains of *G. sulfurreducens* with alterations made to one or more residues of an amino acid sequence corresponding to pilin monomer pilA protein. Strains include strain W51W57 (S1), strain MP (*G. metallireducens*; S2), strain DL1; ATCC 51573 (WT *G. sulfurreducens*; S3) and strain Aro5 (S4).

According to some embodiments, tryptophan (W) may replace the last two aromatic residues, as in strain S1. Tyrosine (Y) is present in strains S1-S3, and phenylalanine (F) is present in all strains S1-S4. In S4, the last 5 aromatic residues were replaced by Alanine. As will be described in discussion of FIG. 4, the removal of aromatic residues in strain S4 represses the expression of pilA proteins and OmcS on the outer surface of the bacterium.

In addition to *G. sulfurreducens*, the inventors have appreciated and recognized that many other strains of bacteria exhibit cytochrome and pili protein production and have been observed to produce conductive nanowires. FIG. 2B lists several strains of bacteria with alterations made to one or more residues of an amino acid sequence corresponding to pilin monomers, including but not limited to *Neisseria gonorrhoeae, Neisseria meningitidis, Pseudomonas aeruginosa, Esherasease* and *Shewanella oneidensis* (not pictured). According to some embodiments, nanowires expressed from these bacteria include but are not limited to pilA nanowires, pilE nanowires (*Neisseria*), and fimA nanowires (*Escherichia*).

The inventors have appreciated and recognized that bacterial adhesion to the host-cell is often the first step in most infections. Bacteria also adhere to each other to form biofilms, which occur in 80% of microbial infections, block the efficacy of most anti-microbials, and result in chronic infection and the need for surgical removal of afflicted areas. Because the surfaces of both bacteria and host are negatively charged, the ligands located on the bacterial nanowires allow for initial adhesion to host-cell receptors without bacteria getting close enough for electrostatic repulsion. However, it is unclear what mechanisms eliminate the electrostatic repulsion when nanowires retract and bacteria achieve close adhesion to the host. *Pseudomonas aeruginosa, Neissseria gonorrhoeae* and *Neisseria meningitidis* may produce conductive nanowires due to closely packed aromatic amino acids in pili proteins.

Figure 3:
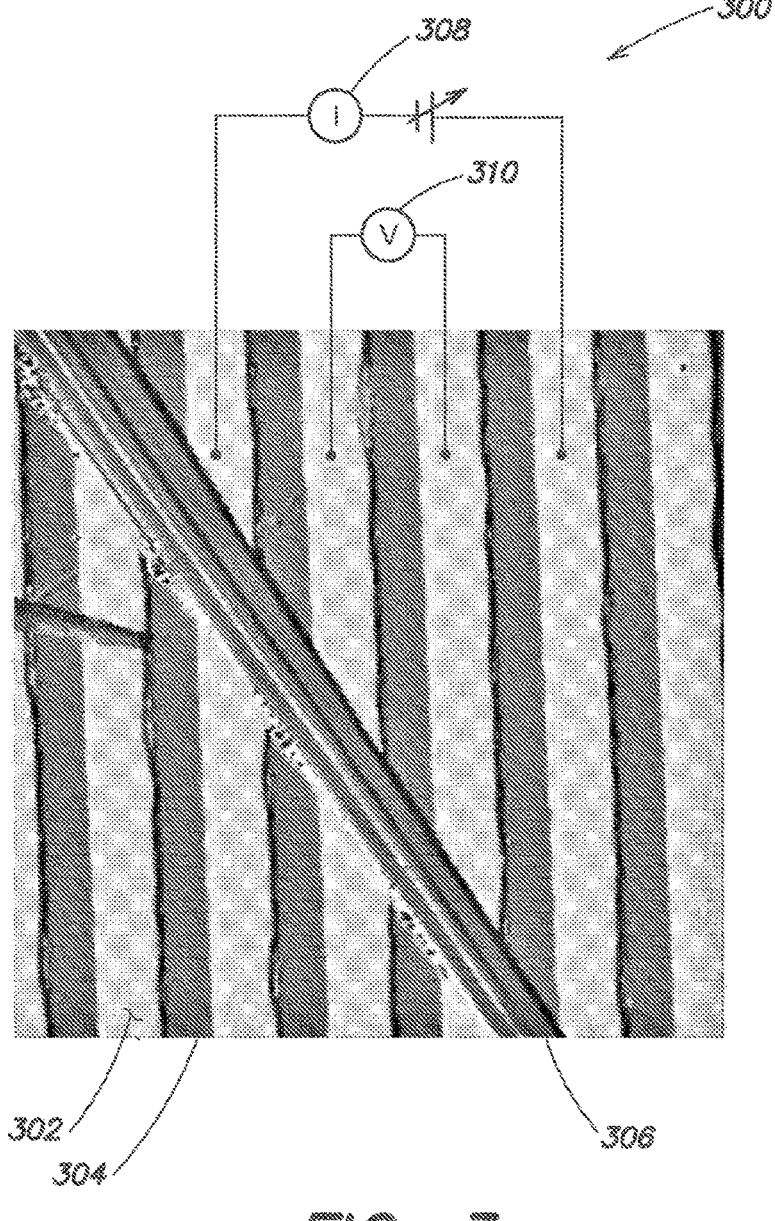
FIG. 3 illustrates a device for making 4-terminal conductivity measurements of a nanowire.

As discussed previously, conventional techniques of measuring conductivity in synthetic nanowires may result in inaccurate conductivity measurements of nanowires comprising proteins. Conventional 2-terminal conductivity measurements may be prone to artifacts such as contact resistance. FIG. 3 depicts an apparatus 300 for making 4-terminal conductivity measurements of a cytochrome or other protein nanowire.

In some embodiments, the apparatus 300 comprises gold electrodes 302 which may be separated by a 300 nm non-conductive gap 304. Nanowires 306 may then be isolated from bacteria and placed on the apparatus 300 so that they bridge four electrodes. A current (I) may be injected through the outer two electrodes and a DC voltage (V) may be measured through the inner two electrodes. As no current can flow through the inner circuit due to the high input impedance of the voltmeter, this method enables measurement of the intrinsic conductivity of pili without any contributions from contact resistance.

Figure 4:
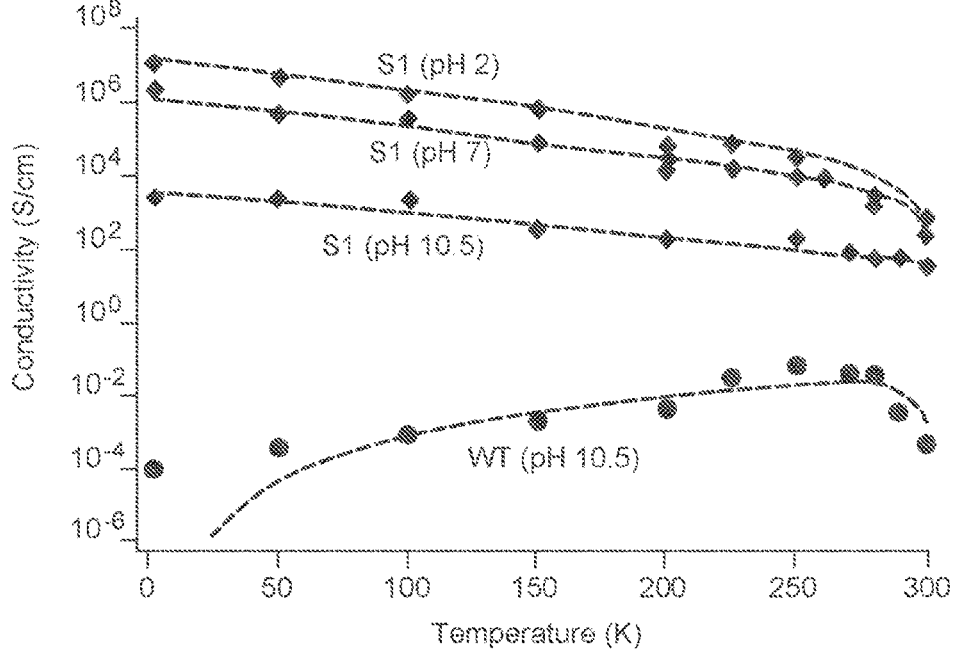
FIG. 4 illustrates 4-terminal conductivity measurements over a range of temperatures of nanowires from different *Geobacter* strains.

The apparatus 300 may be operated across a range of temperatures and pH levels. FIG. 4 shows temperature dependent conductivity measurements of *Geobacter* nanowires from strains S1 and S3 at various pH levels. A change in pH may induce structural changes in the nanowires that increases electronic conductivity and mechanical stiffness. Insulating and semiconducting materials exhibit a decrease in conductivity with a decrease in temperature, while metallic materials exhibit an increase in conductivity with a decrease in temperature.

The conductivity of nanowires strain S3 increased upon cooling near physiological temperatures, indicating metallic behavior. However, the conductivity then decreased at lower temperatures, indicating a crossover to semiconducting behavior. The strain S1 produces nanowires with very high conductivity at room temperature that increased exponentially upon cooling, all the way down to 2 K, in a manner similar to that evident with metallic carbon nanotubes. Lowering the pH of nanowires from strain S1 further increased their conductivity and improved their metallic nature due to conformational changes in the protein structure and heme stacking.

Figure 5A:
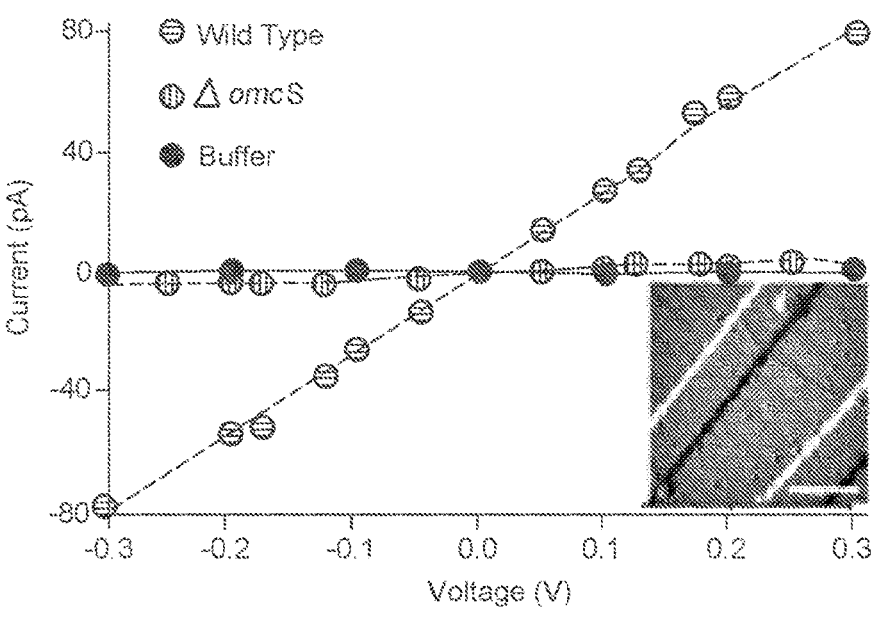
FIG. 5A illustrates current-voltage curves of nanowires from wild type and ΔomcS strains of *Geobacter;*

A comparison may further be made between protein nanowires from *G. sulfurreducens* WT strain S3 (DL1; ATCC 51573) and an omcS deletion mutant strain (ΔomcS). *G. sulfurreducens* forms a variety of nanowires in response to genetic mutations, and the ΔomcS strain forms nanowires that were previously thought to be conductive type IV pili. FIG. 5A depicts current-voltage (I-V) curves of nanowires produced by each of the aforementioned strains as well as a control curve from the buffer solution.

According to some embodiments, DC conductivity measurements of nanowires may be performed under fully hydrated buffer conditions in a 2-electrode configuration. A DC voltage, typically in the range of –0.5V to +0.5V, may be applied between the two electrodes and the current may be measured over a minimum period of 120 seconds until a steady state is achieved. Measurements were performed at low voltages (<0.5 V) and over longer times (>100 seconds) to ensure a lack of electrochemical leakage currents or faradic currents as evidenced by the absence of significant DC conductivity in buffer or nanowires of ΔomcS strain that were maintained under identical buffer conditions as nanowires of the WT strain.

Figure 5B:
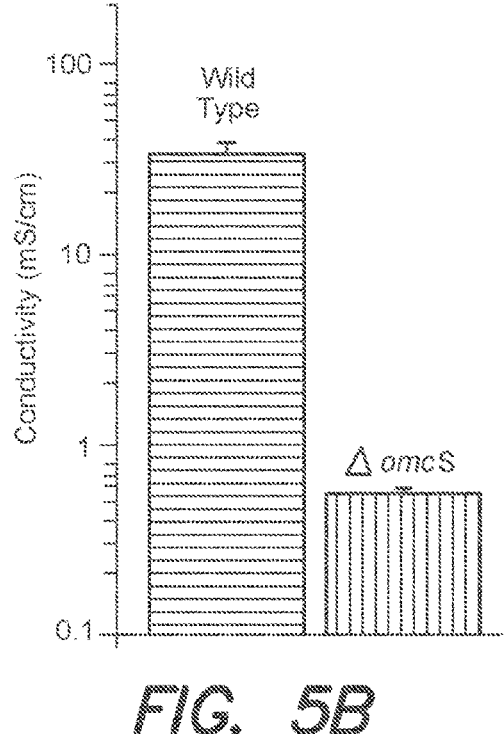
FIG. 5B illustrates conductivities of nanowires from wild type and ΔomcS strains of *Geobacter;*

The linearity of the I-V characteristics may be maintained by applying an appropriate low voltage, and the slope of the I-V curve may be used to determine the conductance (G). The conductivity (σ) of the nanowires may be calculated using the relation $\sigma = G \cdot (L/A)$ where G is the conductance, L is the length of the nanowire, and $A = \pi r^2$ is the area of cross section of nanowire with 2r as the height of the nanowire measured. FIG. 5B depicts DC conductivity measurements comparing nanowires produced by the WT strain and the ΔomcS strain of *G. sulfurreducens* as in FIG. 5A.

According to some embodiments, DC conductivity measurements of individual ΔomcS nanowires showed a very low conductivity that was more than 100-fold lower than OmcS nanowires from a WT strain. The DC conductivity measurements of individual OmcS nanowires fully hydrated in buffer yielded values comparable to previous measurements of WT nanowires in the art, further suggesting that OmcS nanowires are identical to the WT nanowires discussed in previous studies as Type IV pili. These conductivity measurements indicate that OmcS is required for high conductivity of these ~4 nm-thick nanowires.

OmcS may also play a critical role in long-range electron transport to electrodes in current-producing biofilms. Both microarray and quantitative reverse transcription polymerase chain reaction (qRT-PCR) analysis have demonstrated that cells show higher transcript levels for OmcS than for any other protein during the early stages of growth on electrodes. Furthermore, immunogold localization has shown that OmcS is distributed throughout conductive *G. sulfurreducens* biofilms and that deletion of the omcS gene inhibits electricity production. However, the role of OmcS in conductivity may have been overlooked because ΔomcS biofilms were conductive and produced high current densities. These results might be due to a reciprocal relationship between the expression of OmcS and that of OmcZ, a cytochrome essential for current production. The ΔomcS biofilms may compensate for the loss of OmcS by increasing the production of OmcZ.

Figure 5C:
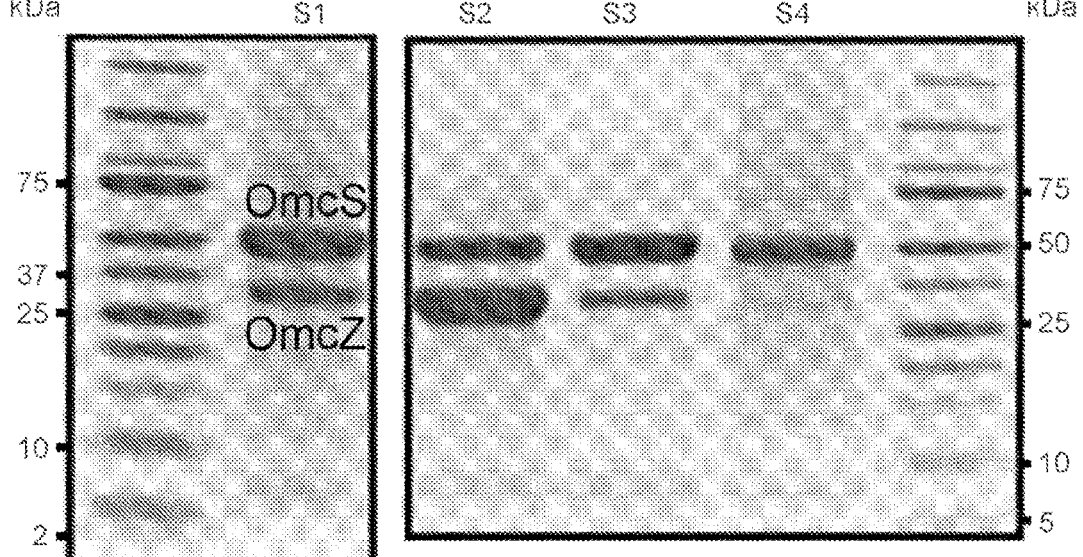
FIG. 5C illustrates polyacrylamide gel electrophoretic separation (SDS-PAGE) images from a subset of *Geobacter* strains.

Further evidence for the relationship between pilA expression and OmcS and OmcZ expression may be seen in the polyacrylamide gel electrophoretic separation (SDS-PAGE) images shown in FIG. 5C. Protein gels were prepared for *Geobacter* strains S1 through S4 of FIG. 2A. Two bands are present for OmcS and OmcZ. The mutations made to the pilA proteins of strains S1 through S4 can be seen to change the expression of OmcS and OmcZ. For example, S4 does not produce any OmcZ whereas S2 strongly produces OmcZ. Thus, tuning the sequence and expression of pilA may allow for tuning the expression of OmcS and OmcZ.

Bacteria other than *G. sulfurreducens* express conductive protein nanowires. For example, the pili proteins of pathogenic bacteria, such as, but not limited to, *Pseudomonas aeruginosa, Neisseria gonorrhoeae, Neisseria meningitidis*, are also electrically conductive. The conductivity and adhesion force of pathogenic pili are correlated with the density and stacking of aromatic amino acids in pili. Targeting electron transfer via pili to reduce bacterial adhesion to the host-cell could have significant impact for the development of new therapies that prevent pathogen adhesion.

Figure 6A:
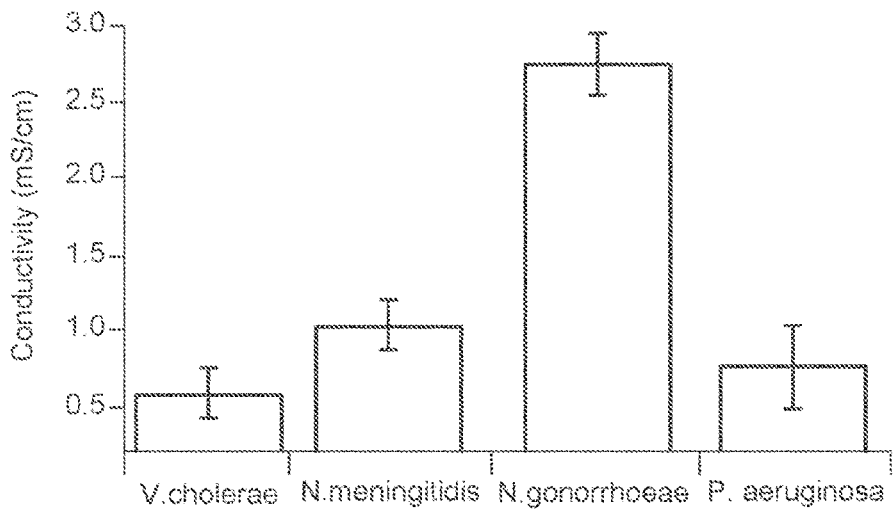
FIG. 6A illustrates measured conductivities of *G. sulfurreducens, P. aeruginosa, N. gonorrhoeae,* and *N. meningitidis* nanowires.

Conductivity measurements are shown in FIG. 6A from nanowires produced by *P. aeruginosa, N. gonorrhoeae, N. meningitidis*, and *V. cholerae*. Nanowires of *N. gonorrhoeae* have a high conductivity of 2-3 mSiemens/cm. From FIG. 2B, the amino acid sequence of *N. gonorrhoeae* comprises aromatics such as tryptophan. In contrast, the nanowires of *V. cholerae*, which lacks closely stacked aromatics as shown in the sequences of FIG. 2B, showed low conductivity.

Based on the atomic structure of type IV pili, closely stacked aromatic residues, phenylalanine (F) and tyrosine (Y), enable electron transfer in pili. These residues are absent in the Type IVb pili found in enteric pathogens such as *V. cholerae* and the aromatics at other locations are too far (>17 Å) from each other for π overlap, suggesting a lack of conductivity in type IVb pili. Bacteria with Type IVa pili show significantly higher adaptability to cause infections than those with Type IVb pili, suggesting that pili conductivity is important in infections.

Figure 6B:
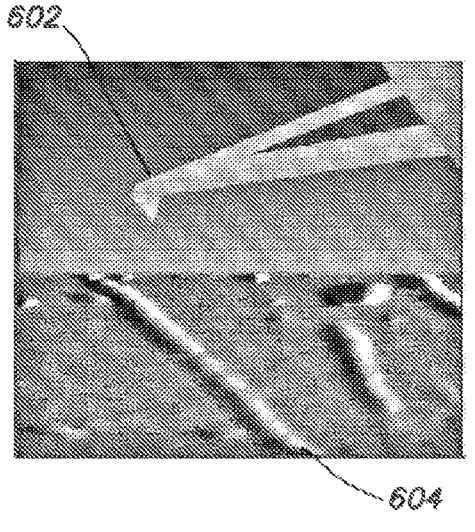
FIG. 6B illustrates an exemplary use of atomic force microscopy to generate a force curve to determine the adhesive force of a protein nanowire.
Figure 6C:
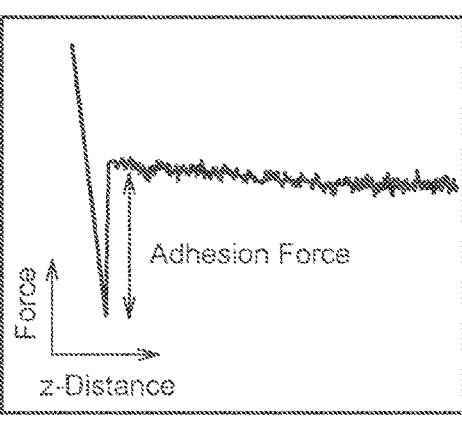
FIG. 6C illustrates an exemplary force curve generated from a protein nanowire by atomic force microscopy.

The force by which a nanowire adheres to a surface may be measured with force spectroscopy using an atomic force microscope. FIG. 6B shows an exemplary atomic force microscope tip 602 above a surface with a nanowire 604. By driving the tip 602 towards the nanowire 604, the tip 602 may contact the nanowire 604. Driving the tip 602 away from the surface while in contact with the nanowire 604 may generate the force vs. distance curve of FIG. 6C. As the tip 602 withdraws from the surface, the tip will measure a negative adhesion force due to the nanowire 604 remaining attached to the surface. At some distance from the surface, the nanowire 604 will release from the surface as the force it experiences from the tip 602 overcomes the nanowire's adhesive force to the surface.

A series of *N. meningitidis* mutant strains with varied density of aromatic residues in their pili were prepared to compare pili conductivity and adhesion capacity via atomic force microscopy. FIG. 6D shows conductivity of *N. meningitidis* pili and FIG. 6E shows adhesion force of *N. meningitidis* pili for a variety of mutant strains. The conductivity and adhesion force may be correlated, indicating overlapping r-orbitals may enable electron transfer. For example, mutating Serine 34 to Tyrosine increased both the conductivity and adhesion by 3-fold. In contrast, mutating Tyrosine 17 to Alanine decreased both the conductivity and adhesion.

A series of conductivity and adhesion force measurements on pili from *P. aeruginosa* under decreasing pH conditions are shown in FIG. 6F and FIG. 6G, respectively. In FIG. 6F, it can be seen that the conductivity of pili is 3-fold higher at pH 5 as compared to at pH 7.2. Pilus adhesion forces in FIG. 6G show the same trend. Measurements were made on flagella as a negative control for the effect of pH on adhesion.

Figure 7:
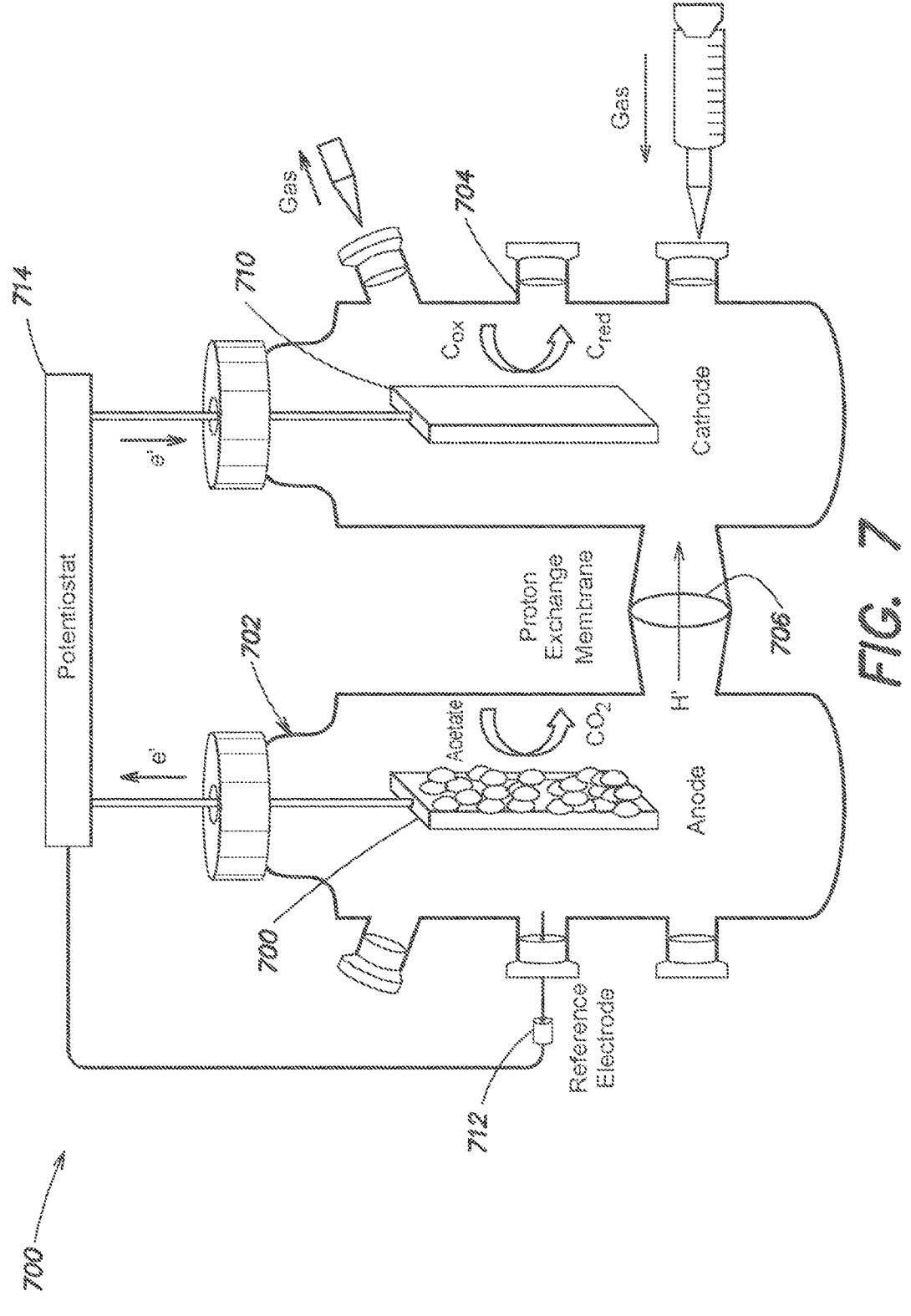
FIG. 7 illustrates an exemplary microbial fuel cell for the manufacture of nanowires expressed by a bacterium.

Bioelectrochemical systems (BES) use microorganisms to catalyze an oxidation and/or reduction reaction at an anodic and/or cathodic electrode, respectively. FIG. 7 depicts an illustrative BES comprising a microbial electrolysis cell (MEC) 700 for the manufacture of cytochrome nanowires according to some embodiments. The MEC 700 may comprise two vessels 702 with three apertures 704 each, which may be connected through a proton exchange membrane 706. An anode 708 and a cathode 710 may be provided in the vessels 702, and a reference electrode 712 may be provided in the vessel 702 containing the anode 708. A potentiostat 714 may maintain a constant electrical potential between the anode 708 and cathode 710.

Vessels 702 may further contain a liquid medium for cell growth. The liquid medium may comprise compounds that may act as electron donors or electron acceptors. One non-limiting example of a compound that may act as an electron acceptor is fumaric acid, or fumarate. The liquid medium may further comprise minerals and vitamins as appropriate to sustain bacterial growth and function.

According to some embodiments, a constant potential may be maintained at the anode 708 so that the bacteria can use the anode 708 as a terminal electron acceptor. The anode 708 and the cathode 710 may comprise any material suitable for use in a BES, including but not limited to graphite. The reference electrode 712 may comprise any material suitable for use in a BES, including but not limited to Ag/AgCl.

The inventors have recognized and appreciated that stimulating the growth of multilayer biofilms comprising cytochrome nanowires may require three different modes of operation of the MEC 700. These three different modes of operation may serve to promote initial growth of the bacterial cells in the MEC 700, to promote biofilm growth on the electrodes, and to promote the growth of multilayer biofilms that can be hundreds of micrometers thick and produce high electric current.

According to some embodiments, bacteria may be grown anaerobically in 1 L cultures of sterilized and degassed NBAF medium comprising 0.04 g/L calcium chloride dihydrate, 0.1 g/L magnesium sulphate heptahydrate, 1.8 g/L sodium bicarbonate, 0.5 g/L sodium carbonate, 0.42 g/L potassium phosphate monobasic, 0.22 g/L potassium phosphate dibasic, 0.2 g/L ammonium chloride, 0.38 g/L potassium chloride, 0.36 g/L sodium chloride, vitamins and minerals, using 20 mM sodium acetate trihydrate as the electron donor and 40 mM fumaric acid as the electron acceptor. Resazurin may be omitted and 1 mM cysteine may be added as an electron scavenger.

According to some embodiments, promoting initial growth of the bacterial cells in the MEC 700 uses fresh water acetate fumarate (FWAF) medium. According to some embodiments, the FWAF medium comprises sodium acetate trihydrate and fumaric acid as well as minerals and vitamins as needed to sustain bacterial growth. The FWAF medium may have a pH of 7.0. During this stage of operation, any suitable voltage may be applied against the reference electrode 712. According to some embodiments, 0.3 V may be applied against the reference electrode 712.

Growth of the initial population of bacteria in the MEC 700 may be monitored by checking the concentration of bacterial cells in the FWAF medium. Upon reaching a suitable concentration which may be able to establish a biofilm, the next stage of operation may begin. Bacterial concentration may be monitored by measuring the optical density measured at a wavelength of 600 nm ($OD_{600}$) of the FWAF medium. According to some embodiments, a suitable $OD_{600}$ for moving to the next stage of operation may be 0.2.

After reaching a desired bacterial concentration, initial biofilm growth on the anode 708 and/or cathode 710 may be promoted. In this stage, fresh water acetate (FWA) medium may be used. According to some embodiments, the FWA medium comprises sodium acetate trihydrate as well as minerals and vitamins as needed to sustain bacterial growth. The FWA medium may have a pH of approximately 7. The FWA medium may lack the soluble electron acceptor fumaric acid. By removing the soluble electron acceptor from the culture medium, the bacteria may be encouraged to grow using the anode as the terminal electron acceptor.

Biofilm growth during this stage of operation may be monitored by monitoring the current flowing through the MEC 700. The current may climb to a maximum and then begin to drop, indicating a decrease in biofilm production. According to some embodiments, the maximum current during this stage of operation may be approximately 0.2 mA.

To encourage the growth of multilayer biofilms for preparation of cytochrome nanowires, a continuous supply of fresh FWA medium may be used to remove planktonic cells in the MEC 700. The FWA medium during this stage of operation may be fortified with further vitamins and minerals to encourage biofilm growth. During this stage of operation of the MEC 700, fresh fortified FWA medium may be pumped through the MEC 700 using a pump such as a peristaltic pump. As described previously, the current flowing through MEC 700 may provide an indication as to biofilm growth on the anode 708. The current may be observed to reach a maximum and thereafter may decrease. The maximum current observed in MEC 700 with *G. sulfurreducens* strain PCA is ~12 mA. Upon reaching a peak current, the biofilm may be ready for removal from the MEC 700.

Figure 8:
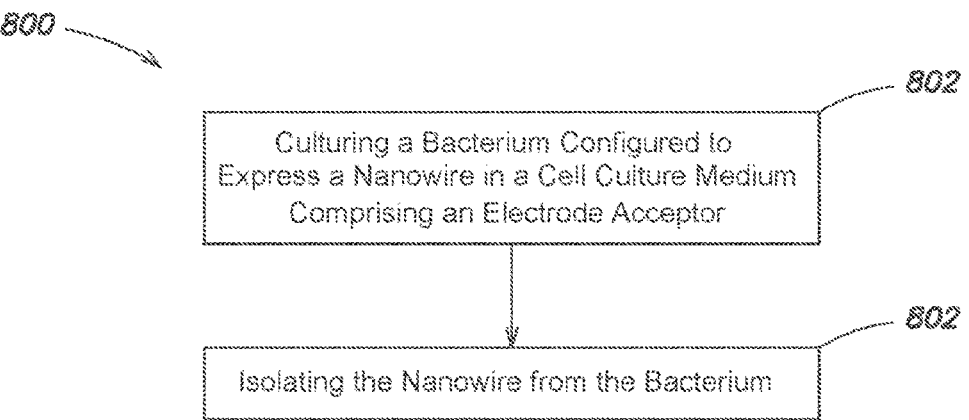
FIG. 8 is a flowchart illustrating the method of manufacture of nanowires expressed by a bacterium.

FIG. 8 is a process flowchart showing steps for the manufacture of nanowires according to some embodiments that are expression products of a bacterium. In act 802, a bacterium which is configured to express a desired nanowire is cultured in a cell culture medium comprising an electron acceptor. The cell culture medium may be any suitable cell culture medium, including but not limited to the cell culture medium of the description of FIG. 7. The electron acceptor may comprise an electrode as in the description of FIG. 7, or any other suitable electron acceptor.

In act 804, the nanowires are isolated from the bacterium using any suitable method known to those with skill in the art. One non-limiting example of isolating the cytochrome nanowires includes centrifuging the cell culture medium to separate the bacteria and the nanowires. According to some embodiments, cells may be gently scraped from the electron acceptor using a plastic spatula and isotonic wash buffer ($20.02 \times 10^{-3}$ M morpholinepropanesulfonic acid, $4.35 \times 10^{-3}$ M $NaH_2PO_4.H_2O$, $1.34 \times 10^{-3}$ M KCl, $85.56 \times 10^{-3}$ M NaCl, $1.22 \times 10^{-3}$ M $MgSO_4.7H_2O$, and $0.07 \times 10^{-3}$ M $CaCl_2).2H_2O$), then collected by centrifugation and resuspended in $150 \times 10^{-3}$ M ethanolamine (pH 10.5). Nanowires may be mechanically sheared from the cell surface using a Waring Commercial Blender (Cat. No. 7011S) at low speed for 1 min. Cells may be removed by centrifugation at 13,000 g before collecting the nanowires with an overnight 10% ammonium sulfate precipitation and subsequent centrifugation at 13,000 g. Collected filaments may be re-suspended in ethanolamine buffer then cleaned by centrifugation at 23,000 g to remove debris. A second 10% ammonium sulfate precipitation with and second centrifugation at 13,000 g may be performed. The final filament preparation may be re-suspended in 200 µl ethanolamine buffer. Further preparation may include passing the nanowires through a filter of any suitable size to remove any remaining cells. The filter may be a 0.2 µm filter.

Figure 9:
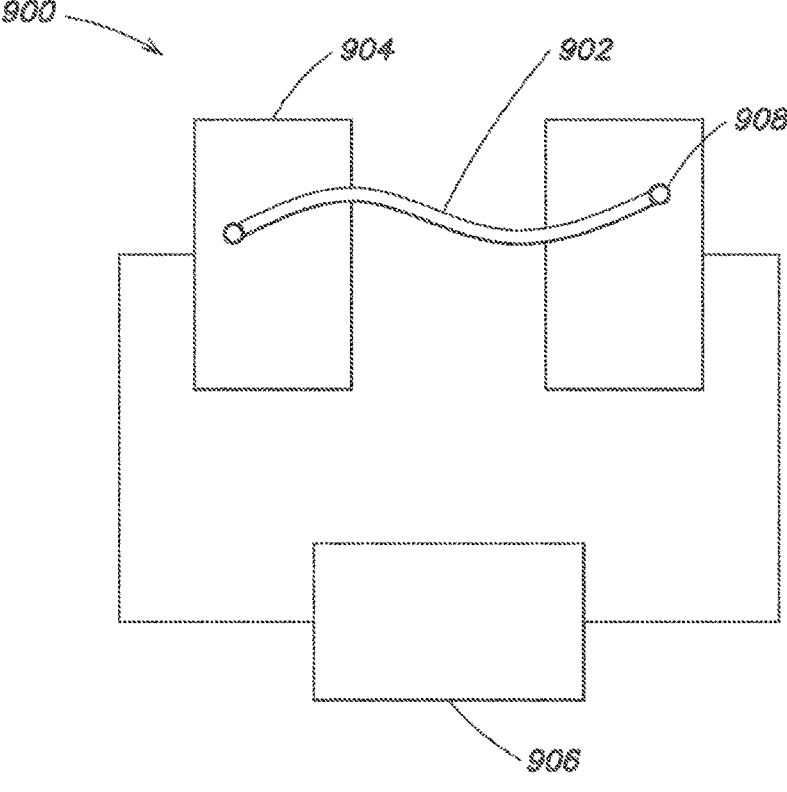
FIG. 9 illustrates an illustrative electronic device comprising a nanowire isolated from a bacterium.

Nanowires such as those described in the present technology may be integrated into electronic devices. FIG. 9 shows an illustrative electronic device 900 comprising an isolated nanowire 902. Some non-limiting examples of applications of electronic device 900 are described herein. Electronic device 900 may be configured for integration into electronic transistors, diodes, integrated circuits, reactive components, and/or electronic sensors of any type and in any combination. Electronic device 900 may be integrated into a complementary metal-oxide-semiconductor (CMOS) chip for applications in sensors or light harvesting devices. Electronic device 900 may be integrated into wearable electronic devices, biological monitors, or any device requiring interfacing between biological and synthetic (i.e. manufactured) systems.

According to some embodiments, electronic device 900 may further comprise at least one electrode 904, suitable circuit components 906, and points of connection 908 between the nanowire 902 and electrodes 904. The isolated nanowire 902 may be any one of the protein nanowires described previously in the present application, including but not limited to cytochrome nanowires, pilA nanowires, pilE nanowires, or fimA nanowires. The points of connection 908 provide electrical coupling between the nanowire 902 and the electrodes 904, and may occur through any suitable means including but not limited to van der Waals forces, tunneling contacts, and coupling to electrodes via cysteines or hemes in nanowires.

The electronic device 900 may comprise any suitable circuit components 908. In some embodiments, circuit components 908 may include a current supply or a voltage supply to supply electrical power to the electronic device 900. Circuit components 908 may include electronic filters or amplifiers to better isolate signal from the nanowire 902. Circuit components 908 may include a voltmeter or ammeter to monitor the electrical behavior of the nanowire 902. The aforementioned components are intended to be a non-limiting set of examples, and any suitable circuit components may be included in electronic device 900 to achieve desired functionality.

Electronic device 900 may be used to form a variety of electronic devices. For example, the nanowire could be used as part of a circuit and incorporated into a resistor, a capacitor, a transistor, a diode, a logic gate, a sensor, a memory and other analog and digital circuits as part of passive or active components in such circuits. According to some embodiments, the electronic device 900 could be part of an integrated circuit. These examples are not meant to be limiting but merely illustrative of the applications of the disclosed technology.

According to some embodiments, electronic device 900 may be used for spin-dependent electronic ("spintronics") applications. The nanowire 902 may have an intrinsic chirality due to its helical structure. The chirality of nanowire 902 may be used to create a spin-polarized transport device based on electronic device 900, as the chiral nature of nanowire 902 may cause induced spin selectivity within the nanowire 902.

According to some embodiments, electronic device 900 may be used for electrolytic (or ionic) gating in 2-dimensional systems. Electrolyte gating techniques employing ionic liquids may provide a means to tune very large carrier densities at the surfaces of a wide variety of materials. Some materials used for electrolytic gating include, but are not limited to, ionic gels and perovskite materials such as $SrTiO_3$, $LaAlO_3$, and $LaSrCoO_3$. Nanowire 902 may be used to transfer charge across the surface of such a material in an electrolytically backgated system.

According to some embodiments, electronic device 900 may be used for electronic sensing applications of molecular biomaterials. Molecular discrimination between individual molecular biomaterials may be achieved by attaching said molecular biomaterials to nanowire 902 and measuring the electronic signal of nanowire 902. This technology may be applicable to a wide array of molecular biomaterials including but not limited to RNA and other proteins, because measuring current through each amino acid may provide unique electronic "fingerprints" associated with their tunneling current.

Furthermore, the present technology can be embodied in the following configurations:

(1) A nanowire comprising a protein from a bacterium, the protein comprising at least one of c-type heme subunits and pili proteins.

(2) The nanowire of (1), wherein the protein is capable of establishing an electrical connection with an insoluble electron acceptor.

(3) The nanowire of any one of (1)-(2), wherein the bacterium is from any one of Geobacteraceae, Shewanellaceae, *Escherichia*, Pseudomonadaceae, and Neisseriaceae.

(4) The nanowire of any one of (2)-(3), wherein the bacterium is from any one of *Geobacter sulfurreducens, Geobacter metallireducens, Shewanella oneidensis, Escherichia coli, Psuedomonas aeruginosa, Neisseria gonorrhoeae,* and *Neisseria meningitidis.*

(5) The nanowire of any one of (2)-(4), wherein the bacterium is from any one of *Geobacter sufurreducens* strains W51W57, MP, CL1, ZKI, OmcS knock-out, OmcZ knock-out, Aro5, and DLI; ATCC 51573.

(6) The nanowire of any one of (1)-(5), wherein the c-type heme subunits are any one of a cytochrome OmcS or OmcZ or any combination thereof.

(7) The nanowire of (6), wherein the cytochrome has a molecular weight between 20 kDa and 60 kDa.

(8) The nanowire of any one of (1)-(7), wherein the bacterium expresses pilin proteins comprising any one of a selection of pilA, pilE, or fimA proteins.

(9) The nanowire of (8), wherein the pilin proteins comprise an amino acid sequence comprising a substitution at at least one amino acid to an aromatic amino acid.

(10) The nanowire of (9), wherein the aromatic amino acid is tryptophan.

(11) The nanowire of (2), wherein the insoluble electron acceptor is any one of an electrode, a second isolated nanowire, or any combination thereof.

(12) The nanowire of any one of (1)-(11), wherein the nanowire has metallic electronic properties.

(13) The nanowire of any one of (1)-(11), wherein the nanowire has semiconducting electronic properties.

(14) A method of preparing a nanowire, comprising:

culturing a bacterium configured to express a nanowire in a cell culture medium comprising an electron acceptor; and isolating the nanowire from the bacterium.

(15) The method of (14), wherein the bacterium is any one of Geobacteraceae, Shewanellaceae, Escherichia, Pseudomonadaceae, and Neisseriaceae.

(16) The method of (15), wherein the bacterium is any one of Geobacter sulfurreducens, Geobacter metallireducens, Shewanella oneidensis, Escherichia coli, Psuedomonas aeruginosa, Neisseria gonorrhoeae, and Neisseria meningitidis.

(17) The method of (16), wherein the bacterium is any one of Geobacter sufurreducens strains W51W57, MP, CL1, ZKI, OmcS knock-out, OmcZ knock-out, Aro5, and DLI; ATCC 51573.

(18) The method of any one of (14)-(17), wherein the nanowire is a pilin protein comprising any one of a selection of pilA, pilE, or fimA proteins.

(19) The method of any one of (14)-(17), wherein the nanowire comprises any one of a c-type cytochrome OmcS or OmcZ or any combination thereof.

(20) The method of any one of (14)-(19), wherein isolating the nanowire comprises:

separating the nanowire from the bacterium.

(21) The method of (18), wherein the pilin proteins comprise an amino acid sequence comprising a substitution at at least one amino acid to an aromatic amino acid.

(22) The method of (21), wherein the aromatic amino acid is tryptophan.

(23) The method of any one of (14)-(22), wherein the electron acceptor is an anode kept at a constant electric potential.

(24) The method of (23), wherein keeping the anode at a constant electric potential comprises using a potentiostat.

(25) The method of any one of (22)-(23), wherein the anode is formed of graphite.

(26) The method of any one of (14)-(25), wherein placing the bacterium in contact with the culture medium occurs in vitro.

(27) The method of any one of (14)-(26), wherein placing the bacterium in contact with the culture medium occurs in an anaerobic environment.

(28) A method of using Geobacteraceae to prepare a cytochrome nanowire, comprising:

culturing a Geobacteraceae bacterium configured to express a cytochrome nanowire in a cell culture medium comprising an electron acceptor; and isolating the cytochrome nanowire from the Geobacteraceae bacterium.

(29) The method of (28), wherein the cytochrome nanowire is any one of a c-type cytochrome OmcS or OmcZ or any combination thereof.

(30) The method of any one of (28)-(29), wherein the bacterium is any one of Geobacter sufurreducens strains W51W57, MP, CL1, ZKI, OmcS knock-out, OmcZ knock-out, Aro5, and DLI; ATCC 51573.

(31) The method of any one of (28)-(30), wherein isolating the cytochrome nanowire comprises:

separating the cytochrome nanowire from the bacterium.

(32) The method of any one of (28)-(31), wherein the cytochrome nanowire is expressed by the bacterium in conjunction with pilA proteins.

(33) The method of (32), wherein the pilA proteins comprise an amino acid sequence comprising a substitution at at least one amino acid to an aromatic amino acid.

(34) The method of (33), wherein the aromatic amino acid is tryptophan.

(35) The method of any one of (28)-(34), wherein the electron acceptor is an anode kept at a constant electric potential.

(36) The method of (35), wherein keeping the anode at a constant electric potential comprises using a potentiostat.

(37) The method of any one of (35)-(36), wherein the anode is formed of graphite.

(38) The method of any one of (28)-(37), wherein placing the bacterium in contact with the culture medium occurs in vitro.

(39) The method of any one of (28)-(38), wherein placing the bacterium in contact with the culture medium occurs in an anaerobic environment.

(40) An electronic device, comprising:

at least one electrode; and a nanowire electrically coupled to the at least one electrode, wherein the nanowire is an expression product of a bacterium.

(41) The electronic device of (40), wherein the bacterium is selected from any one of Geobacteraceae, Shewanellaceae, Escherichia, Pseudomonadaceae, and Neisseriaceae.

(42) The electronic device of (41), wherein the bacterium is selected from any one of Geobacter sulfurreducens, Geobacter metallireducens, Shewanella oneidensis, Escherichia coli, Psuedomonas aeruginosa, Neisseria gonorrhoeae, and Neisseria meningitidis.

(43) The electronic device of (42), wherein the bacterium is from any of Geobacter sufurreducens strains W51W57, MP, DLI; ATCC 51573.

(44) The electronic device of any one of (40)-(43), wherein the nanowire comprises any one of a c-type cytochrome OmcS or OmcZ or any combination thereof.

(45) The electronic device of any one of (40)-(43), wherein the nanowire is a pilin protein comprising any one of a selection of pilA, pilE, or fimA proteins.

(46) The electronic device of (45), wherein the pilin proteins comprise an amino acid sequence comprising a substitution at at least one amino acid to an aromatic amino acid.

(47) The electronic device of (46), wherein the aromatic amino acid is tryptophan.

(48) The electronic device of any one of (40)-(47), wherein the nanowire has metallic electronic properties.

(49) The electronic device of any one of (40)-(48), wherein the nanowire has semiconducting electronic properties.

(50) The electronic device of any one of (40)-(49), wherein the nanowire is prepared in an in vitro culture medium comprising an electron acceptor.

(51) The electronic device of (50), wherein the electron acceptor is an anode kept at a constant electric potential.

(52) The electronic device of any one of (40)-(51), wherein the electronic device is placed within an aqueous environment.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A nanowire obtained by a method comprising:

culturing bacteria capable of expressing a protein comprising c-type cytochrome subunits arranged in a helical structure in a first cell culture medium comprising a soluble electron acceptor in a microbial electrolysis cell, wherein heme groups of the c-type cytochrome subunits are arranged to form a heme backbone of the protein, and the heme backbone comprises a plurality of stacked heme pairs;

applying a voltage against a reference electrode of the microbial electrolysis cell;

after a desired bacteria concentration is attained in the first cell culture medium, exchanging the first cell culture medium with a second cell culture medium lacking a soluble electron acceptor;

removing a biofilm formed by the bacteria in the second cell culture medium and on an anode of the microbial electrolysis cell; and separating the nanowire from the biofilm by one or more of centrifugation, blending, and/or filtering the second cell culture medium to isolate the protein expressed by the bacteria.

2. The nanowire of claim 1, wherein the bacteria are from any one of families Geobacteraceae, Shewanellaceae, Pseudomonadaceae, and Neisseriaceae or is from genus *Escherichia*.

3. The nanowire of claim 2, wherein the bacteria are any one of *Geobacter sulfurreducens, Geobacter metallireducens, Shewanella oneidensis, Escherichia coli, Pseudomonas aeruginosa, Neisseria gonorrhoeae*, and *Neisseria meningitidis*.

4. The nanowire of claim 1, wherein the c-type cytochrome subunits are OmcS and/or OmcZ.

5. The nanowire of claim 4, wherein the c-type cytochrome subunits have a molecular weight between 20 kDa and 60 kDa.

6. The nanowire of claim 1, wherein the voltage applied against the reference electrode is 0.3V.

7. The nanowire of claim 1, wherein an optical density measured at a wavelength of 600 nm ($OD_{600}$) of the first cell culture medium at the desired bacteria concentration for biofilm production is 0.2.

8. The nanowire of claim 1, wherein the microbial electrolysis cell comprises:

a first vessel containing the anode, the reference electrode, and, during operation of the microbial electrolysis cell, the first or second cell culture medium;

a second vessel containing a cathode and, during operation of the microbial electrolysis cell, the first or second cell culture medium;

a proton exchange membrane connecting the first and second vessels; and a potentiostat connecting the first and second vessels.

9. The nanowire of claim 1, wherein the protein is capable of establishing an electrical connection with an insoluble electron acceptor.

10. The nanowire of claim 1, in combination with an insoluble electron acceptor comprising an electrode or a second isolated nanowire, wherein the nanowire is in electrical contact with the insoluble electron acceptor.

11. A method of preparing a nanowire, comprising:

culturing, in a first cell culture medium comprising an electron acceptor, a bacterium capable of expressing a protein comprising c-type cytochrome subunits arranged in a helical structure, wherein heme groups of the c-type cytochrome subunits are arranged to form a heme backbone of the protein, in a microbial electrolysis cell;

applying a voltage against a reference electrode of the microbial electrolysis cell;

after a desired bacteria concentration is attained in the first cell culture medium, exchanging the first cell culture medium with a second cell culture medium lacking a soluble electron acceptor;

removing a biofilm formed by the bacterium in the second cell culture medium and on an anode of the microbial electrolysis cell; and isolating the nanowire from the biofilm.

12. The method of claim 11, wherein the bacterium is from any one of families Geobacteraceae, Shewanellaceae, Pseudomonadaceae, and Neisseriaceae or is from genus *Escherichia*.

13. The method of claim 12, wherein the bacterium is any one of *Geobacter sulfurreducens, Geobacter metallireducens, Shewanella oneidensis, Escherichia coli, Pseudomonas aeruginosa, Neisseria gonorrhoeae*, and *Neisseria meningitidis*.

14. The method of claim 11, wherein the c-type cytochrome subunits are OmcS and/or OmcZ.

15. The method of claim 11, wherein the microbial electrolysis cell comprises:

a first vessel containing the anode, the reference electrode, and, during operation of the microbial electrolysis cell, the first or second cell culture medium;

a second vessel containing a cathode and, during operation of the microbial electrolysis cell, the first or second cell culture medium;

a proton exchange membrane connecting the first and second vessels; and a potentiostat connecting the first and second vessels.

16. The method of claim 11, wherein the method of isolating the nanowire from the biofilm is performed by one or more of centrifugation, blending, and/or filtering the second cell culture medium.

17. The method of claim 11, wherein the voltage applied against the reference electrode is 0.3V.

18. The method of claim 11, wherein an optical density measured at a wavelength of 600 nm ($OD_{600}$) of the first cell culture medium at the desired bacteria concentration for biofilm production is 0.2.

\* \* \* \* \*